United States Patent
Wätzig et al.

(10) Patent No.: US 10,888,555 B2
(45) Date of Patent: *Jan. 12, 2021

(54) PHARMACEUTICAL COMPOSITION CONTAINING NICOTINIC ACID AND/OR NICOTINAMIDE FOR BENEFICIALLY INFLUENCING BLOOD LIPID LEVELS BY MODIFYING THE INTESTINAL MICROBIOTA

(71) Applicant: CONARIS RESEARCH INSTITUTE AG, Kiel (DE)

(72) Inventors: Georg Wätzig, Kiel (DE); Dirk Seegert, Dänischenhagen (DE)

(73) Assignee: CONARIS RESEARCH INSTITUTE AG, Kiel (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,410

(22) PCT Filed: Dec. 12, 2014

(86) PCT No.: PCT/EP2014/077646
§ 371 (c)(1),
(2) Date: Jun. 10, 2016

(87) PCT Pub. No.: WO2015/086843
PCT Pub. Date: Jun. 18, 2015

(65) Prior Publication Data
US 2017/0027924 A1    Feb. 2, 2017

(30) Foreign Application Priority Data

Dec. 13, 2013 (EP) .................................... 13197283
Feb. 10, 2014 (EP) .................................... 14154543

(51) Int. Cl.
| | | |
|---|---|---|
| A61K 31/455 | (2006.01) |
| A61K 9/00 | (2006.01) |
| A61K 9/50 | (2006.01) |
| A61K 9/48 | (2006.01) |
| A61K 45/06 | (2006.01) |

(52) U.S. Cl.
CPC .......... *A61K 31/455* (2013.01); *A61K 9/0031* (2013.01); *A61K 9/0053* (2013.01); *A61K 9/4891* (2013.01); *A61K 9/5026* (2013.01); *A61K 9/5047* (2013.01); *A61K 9/5073* (2013.01); *A61K 45/06* (2013.01)

(58) Field of Classification Search
CPC .. A61K 31/455; A61K 9/5047; A61K 9/4891; A61K 9/5073; A61K 9/5026; A61K 9/0053; A61K 45/06; A61K 9/0031; A61P 9/00; A61P 3/06
See application file for complete search history.

(56) References Cited

U.S. PATENT DOCUMENTS

| | | | |
|---|---|---|---|
| 6,129,930 A | * | 10/2000 | Bova ................ A61K 9/2027 424/464 |
| 6,713,057 B1 | * | 3/2004 | Chatterjee ............ G01N 33/92 424/94.6 |
| 2005/0063902 A1 | | 3/2005 | Zeligs |
| 2005/0159396 A1 | | 7/2005 | Harty |
| 2006/0264409 A1 | | 11/2006 | Harty |
| 2008/0108684 A1 | | 5/2008 | Matsumoto et al. |
| 2008/0113031 A1 | | 5/2008 | Moodley et al. |
| 2009/0104171 A1 | | 4/2009 | Pardee et al. |
| 2010/0086588 A1 | | 4/2010 | Forbes |
| 2015/0126462 A1 | | 5/2015 | Waetzig et al. |
| 2016/0136147 A1 | | 5/2016 | Højgaard et al. |
| 2016/0317557 A1 | | 11/2016 | Waetzig et al. |

FOREIGN PATENT DOCUMENTS

| | | |
|---|---|---|
| JP | 2011-121889 A | 6/2011 |
| JP | 2012-102054 A | 5/2012 |
| WO | WO 97/28801 A1 | 8/1997 |
| WO | WO 97/29760 A1 | 8/1997 |
| WO | WO 98/02148 A2 | 1/1998 |
| WO | WO 02/11725 A1 | 2/2002 |
| WO | WO 2004/066910 A2 | 8/2004 |
| WO | WO 2005/115075 A2 | 12/2005 |
| WO | WO 2008/044099 A1 | 4/2008 |
| WO | WO 2009/131537 | 10/2009 |
| WO | WO 2009/131537 A1 | 10/2009 |
| WO | WO 2009/149058 A2 | 12/2009 |
| WO | WO 2012/090224 A1 | 7/2012 |
| WO | WO 2017/184563 | 10/2017 |

OTHER PUBLICATIONS https://www.myvmc.com/anatomy/gastrointestinal-system/; 2006.*
Norwich Pharmaceuticals, Inc., "Niaspan®," Prescribing information, Mar. 2013, retrieved from the Internet: http://www.rxabbvie.com/pdf/niaspan.pdf.
Hashimoto et al., "ACE2 links amino acid malnutrition to microbial ecology and intestinal inflammation," Nature, vol. 487, No. 7408, pp. 477-481, Jan. 2012.
Caesar et al., "Effects of gut microbiota on obesity and atherosclerosis via modulation of inflammation and lipid metabolism," Journal of Internal Medicine, vol. 268, No. 4, pp. 320-328, Oct. 2010.
International Search Report dated Jun. 19, 2015 in application No. PCT/EP2014/077646.
Koren et al., "Human oral, gut, and plaque microbiota in patients with atherosclerosis," PNAS, vol. 108, Suppl. 1, pp. 4592-4598, Mar. 2011.
Ott et al., "Detection of Diverse Bacterial Signatures in Atherosclerotic Lesions of Patients with Coronary Heart Disease," Circulation, vol. 113, pp. 929-937, Feb. 2006.

(Continued)

Primary Examiner — Sahar Javanmard
(74) Attorney, Agent, or Firm — Foley & Lardner LLP

(57) ABSTRACT

The present invention relates to a new pharmaceutical composition containing nicotinic acid and/or nicotinamide and/or related compounds for beneficially influencing the intestinal microbiota and blood lipid levels. In certain embodiments, the pharmaceutical composition is partially or entirely released into the lower small intestine and/or large intestine.

30 Claims, 6 Drawing Sheets

Specification includes a Sequence Listing.

(56) References Cited

OTHER PUBLICATIONS

Vrieze et al., "The environment within: how gut microbiota may influence metabolism and body composition," Dibetologia, vol. 53, pp. 606-613, Jan. 2010.
Wahlberg et al., "Effects of nicotinic acid on serum cholesterol concentrations of high density lipoprotein subfractions $HDL_2$ and $HDL_3$ in hyperlipoproteinaemia," Journal of Internal Medicine, vol. 228, pp. 151-157, 1990.
Mckenney et al., "Effect of Niacin and Atorvastatin on Lipoprotein Subclasses in Patients with Atherogenic Dyslipidemia," Am. J. Cardiol., vol. 88, pp. 270-274, Aug. 2001.
Elam et al., "Effect of Niacin on Lipid and Lipoprotein Levels and Glycemic Control in Patients with Diabetes and Peripheral Arterial Disease," JAMA, vol. 284, No. 10, pp. 1263-1270, Sep. 2000.
Seed et al., "The effect of nicotinic acid and acipimox on liporprotein(a) concentration and turnover," Atherosclerosis, vol. 101, pp. 61-68, 1993.
Wan et al., "Advances in the research of niacin deficiency," J. Pract. Dermatolol., vol. 4, No. 4, pp. 219-222, Dec. 2011.
Office Action dated Sep. 26, 2016 in Chinese application No. 201380031622.4.
Bettenworth et al., "Nicotinamide Ameliorates the Course of Citrobacter Rodentium-Induced Colitis Through Enhanced Bacterial Killing," Gastroenterology, vol. 142, No. 5, p. S685, May 2012.
Lu et al., "Pellagra in an Immunocompetent Patient with Cytomegalovirus Colitis," Am. J. Gastroenterol., vol. 96, pp. 932-934, 2001.
Penberthy, "Pharmacological Targeting of IDO-Mediated Tolerance for Treating Autoimmune Disease," Curr. Drug Metab., vol. 8, pp. 245-266, 2007.
Sanchez-Fidalgo, "PARP inhibition reduces acute chronic inflammation in rats," Eur. J. Pharmacol., vol. 563, pp. 216-223, 2007.
Filippi et al., "Nutritional Deficiencies in Patients with Crohn's Disease in Remission," Inflamm. Bowel Disease, vol. 12, pp. 185-191, 2006.
Glenn et al., "Synthesis and Mass Spectrometry of Some Structurally Related Nicotinoids," J. Org. Chem., vol. 43, No. 14, pp. 2860-2870, 1978.
Dominiak et al., "Effects of Nicotine and its Major Metabolites on Blood Pressure in Anaesthetized Rats," Klin. Wochenschr., vol. 63, pp. 90-92, 1985.
Clayton et al., "Pellagra with colitis due to a defect in tryptophan metabolism," Eur. J. Pediatr., vol. 150, pp. 498-502, 1991.
Osman et al., "Bifidobacterium infantis strains with and without a combination of Oligofructose and Inulin (OFI) attenuate inflammation in DSS-induced colitis in rats," BMC Gastroenterology, vol. 6, No. 31, doi: 10.1186/1471-230X/6/31, Oct. 28, 2006.
Mazmanian et al., "A microbial symbiosis factor prevents intestinal inflammatory disease," Nature, vol. 453, pp. 620-625, May 29, 2008.
Segal et al., "Rectal manifestations of pellagra," Intl. Journal of Colorectal Disease, vol. 1, pp. 238-243, 1986.
Frank et al., "Molecular-phylogenetic characterization of microbial community imbalances in human inflammatory bowel diseases," PNAS, vol. 103, No. 34, pp. 13780-13785, Aug. 21, 2007.
International Search Report dated Jul. 16, 2013 in application No. PCT/EP2013/062363 , (corresponding to US 2015/0126462).
European Search Report dated Feb. 19, 2014 in application No. EP 13197261 (corresponding to US 2015/0126462).
Office Action dated May 6, 2016 in U.S. Appl. No. 14/407,780 (US 2015/0126462).
Office Action dated Apr. 21, 2017 in U.S. Appl. No. 14/407,780 (US 2015-0126462).
Office Action dated Nov. 10, 2016 in U.S. Appl. No. 14/407,780 (US 2015-0126462).
Sanyal et al., "Niacin and Laropiprant," Drugs of Today, vol. 46, No. 6, pp. 371-378, Jun. 2010.
Nainggolan, "Niacin/Laropiprant Products to Be Suspended Worldwide," Medscape Medical News, http://www.medscape.com/viewarticle/777519_print, Jan. 2013, retrieved Apr. 9, 2017.

drugs.com, "Prostaglandin D2 antagonists," https://www.drugs.com/drug-class/prostaglandin-d2-antagonists.html. retrieved Apr. 9, 2017.
Williams, "Does smoking tobacco fulfill a nutritional need?," http://newmediaexplorer.org/sepp/2012/01/25/does_smoking_tobacco_fulfill_a_nutritional_need.htm, retrieved Oct. 27, 2016.
Benowitz et al., "Nicotine Chemistry, Metabolism, Kinetics and Biomarkers," Handbook Exp. Pharmacol., vol. 192, pp. 29-60, Oct. 2009.
Sids Initial Assessment Report, "3-Pyridinecarboxamide (nicotinamide)," UNEP Publications, pp. 1-19, Oct. 2002.
European Food Safety Authority, "Tolerable Upper Intake Levels for Vitamins and Minerals," Scientific Committee on Food, Scientific Panel on Dietic Products, Nutrition and Allergies, pp. 121-133, Feb. 2006.
Final Office Action issued in co-pending U.S. Appl. No. 15/103,406, dated Aug. 31, 2017 (US 2016/0317557).
Non-Final Office Action issued in co-pending U.S. Appl. No. 15/103,406, dated Mar. 16, 2017 (US 2016/0317557).
Restriction Requirement issued in co-pending U.S. Appl. No. 15/103,406, dated Jan. 5, 2017 (US 2016/0317557).
Abdu-Allah, et al., "Synthesis of Trigonelline and Nicotinamide Linked Prodrugs of 5-aminosalicylic acid (5-ASA) with Analgesic and Anti-Inflammatory Effects," *Bulletin of Pharmaceutical Sciences, Assiut University*, vol. 28, No. 2, pp. 237-253 (2005).
Kim et al., "L-Tryptophan exhibits therapeutic function in a porcine model of dextran sodium sulfate (DSS)-induced colitis," *Journ. of Nutritional Biochemistry*, vol. 21, pp. 468-475 (2010).
Functions of Vitamin B3, Common Knowledge of Nutrition 1-17 Jan. 1, 2000 http://www.dharmazen.org/X1Chinese/D32Health/H208VitB3.htm [Sections 1 and 6].
Betterworth, "Nicotinamide Ameliorates the Course of Citrobacter Rodentium-Inducted Colitis Through Enhanced Bacterial Killing," Gastroenterology, vol. 142, No. 5, p. S658 (May 2012).
Andrews et al., "Mesalazine (5-aminosalicylic acid) Alters Faecal Bacterial Profiles, but not Mucosal Proteolytic Activity in Diarrhea-Predominant Irritable Bowel Syndrome", AP&T Alimentary Pharmacology and Therapeutics (2011) vol. 34, pp. 374-383.
Gopal et al., "Transport of Nicotinate and Structurally Related Compounds by Human SMCT1 (SLC5A8) and Its Relevance to Drug Transport in the Mammalian Intestinal Tract", Pharmaceutical Research, (Mar. 2007) vol. 24, No. 3, pp. 575-584.
Lawrance, "Topical Agents for Idiopathic Distal Colitis and Proctitis", Journal of Gastroenterology and Hepatology (2011) vol. 26., pp. 36-43.
Marriott et al., "Pharmaceutical Compounding and Dispensing" (2005)pp. 1-305.
Office Action dated Jan. 30, 2018 in U.S. Appl. No. 15/103,406 (US 2016-0317557).
Office Action dated Feb. 7, 2018 in U.S. Appl. No. 14/407,780 (US 2015-0126462).
Office Action dated Feb. 12, 2018 in U.S. Appl. No. 15/103,406 (US 2016/0317557).
Tiwari et al., "Drug Delivery Systems: An Updated Review", Int. J. Pharm Investig. (2012) vol. 2, No. 1, pp. 2-11.
Bays et al., "Safety of Niacin and Simvastatin Combination Therapy," The American Journal of Cardiology, vol. 101, Issue 8, Supplement, pp. S3-S8 (2008).
Cheng et al., "Antagonism of the prostaglandin D2 receptor 1 suppresses nicotinic acid-induced vasodilation in mice and humans," PNAS, vol. 103, No. 17, pp. 6682-6687 (Apr. 2006).
Damman et al., "Salicylates and the Microbiota: A New Mechanistic Understanding of an Ancient Drug's Role in Dermatological and Gastrointestinal Disease," Drug Development Research, vol. 74, pp. 344-352 (2013).
Lai et al., "Suppression of Niacin-induced Vasodilation with an Antagonist to Prostaglandin d2 Receptor Subtype 1," Clinical Pharmacology & Therapeutics , vol. 81. No. 6, pp. 849-857 (Jun. 2007).
Notice of Reasons for Rejection dated Mar. 27, 2018 in Japanese Application No. 2015-516627.

(56) References Cited

OTHER PUBLICATIONS

Oberwittler et al., "Clinical evidence for use of acetyl salicylic acid in control of flushing related to nicotinic acid treatment," The International Journal of Clinical Practice, vol. 60, Issue 6, pp. 707-715 (Jun. 2006).
Office Action dated Aug. 9, 2018 in U.S. Appl. No. 15/103,406 (US 2016-0317557).
Williams et al., "Optimizing clinical use of mesalazine (5-aminosalicylic acid) in inflammatory bowel disease," Therapeutic Advances in Gastroenterology, vol. 4, No. 4, pp. 237-248 (2011).
Office Action dated Aug. 27, 2018 in U.S. Appl. No. 14/407,780 (US 2015-0126462).
Fangmann et al., "Targeted Microbiome Intervention by Microencapsulated Delayed-Release Niacin Beneficially Affects Insulin Sensitivity in Humans," Diabetes Care, vol. 41, pp. 398-405 (Mar. 2018).
Notice of Allowance dated May 20, 2019 in U.S. Appl. No. 14/407,780 (US 2015-0126462).
Office Action dated May 30, 2019 in U.S. Appl. No. 15/103,406 (US 2016-0317557).
Perrie et al., "Controlling Drug Delivery," FASTtrack Pharmaceutics: Drug Delivery and Targeting, second edition, chapter 1 (2012).
Schacht et al., "Polymers for colon specific drug delivery," Journal of Controlled Release, vol. 36, pp. 327-338 (1996).
Office Action dated Oct. 8, 2019 in U.S. Appl. No. 15/103,406 (US 2016-0317557).

\* cited by examiner

```
                         SEQUENCE LISTING

<160> NUMBER OF SEQ ID NOS: 15

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other

<400> SEQUENCE: 1
cctacgggng gcwgcag                                                        17

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggactachvg ggtwtctaat                                                     20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgccagcagc cgcggtaata c                                                   21

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcacaagcag tggagt                                                         16

<210> SEQ ID NO 5
<211> LENGTH: 18
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 5
cttcctccgt tttgtcaa                                                    18

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
agggttgcgc tcgtt                                                       15

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgctacttg aggagga                                                     17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagccgtagc ctttcact                                                    18

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gtgccagcag ccgcggtaat acg                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aacgctagct acaggcttaa ca                                               22

<210> SEQ ID NO 11
<211> LENGTH: 19
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 11
acgctacttg gctggttca                                                    19

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
caatattcct cactgctgcc tcccgta                                           27

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agagtttgat cctggctcag                                                   20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
attaccgcgg ctgctgg                                                      17

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ctgatggagc aacgccgcgt                                                   20
```

PHARMACEUTICAL COMPOSITION CONTAINING NICOTINIC ACID AND/OR NICOTINAMIDE FOR BENEFICIALLY INFLUENCING BLOOD LIPID LEVELS BY MODIFYING THE INTESTINAL MICROBIOTA

SEQUENCE LISTING

The instant application contains a Sequence Listing which has been submitted electronically in ASCII format and is hereby incorporated by reference in its entirety. Said ASCII copy, created on Sep. 23, 2016, is named 052209-0214_SL.txt and is 3,961 bytes in size.

FIELD OF THE INVENTION

The present invention relates to a new pharmaceutical composition containing nicotinic acid and/or nicotinamide and/or related compounds for beneficially influencing blood lipid levels by causing changes in the intestinal microbiota, wherein the pharmaceutical composition is specifically released (e.g., selectively released) into the lower small intestine and/or large intestine.

BACKGROUND

Many inflammatory diseases of the intestinal wall are caused or influenced by changes in the intestinal microbiota and/or an impaired interaction between the intestinal microbiota and the intestines. Such intestinal inflammations occur in humans, e.g., inflammatory bowel diseases (IBD), such as Crohn's disease or ulcerative colitis, but also in other mammals (e.g., chronic idiopathic colitis in dogs). These diseases are based on complex immunological processes which are not fully understood.

However, changes in, and impaired interactions of, the intestinal microbiota can also be causative factors in a number of other diseases. Examples include atopic diseases, such as atopic eczema, allergic conditions or asthma (see e.g., Bisgaard et al. 2011, J. Allergy Clin. Immunol. 128:646; Iebba et al. 2011, Dig. Dis. 29:531; Abrahamsson et al. 2012, J. Allergy Clin. Immunol. 129:434; Candela et al. 2012, BMC Microbiol. 12:95; Olszak et al. 2012, Science 336:489), as well as metabolic diseases with an inflammatory component, such as arteriosclerosis with resulting coronary heart diseases, adiposity or diabetes (Ott et al. 2006, Circulation 113:929; Koren et al. 2011, PNAS 108 Suppl 1:4592; for reviews see Caesar et al. 2010, J. Intern. Med. 268:320; and Vrise et al. 2010, Diabetologia 53:606).

Although the relationship between the intestinal microbiota and various diseases is known, it has not been understood how to influence the microbiota in a way that would have a beneficial impact on associated diseases.

Therapy of lipid metabolism disorders with statins is highly efficient in reducing cardiovascular morbidity and mortality. However, even in large statin trials aiming at primary or secondary prevention (e.g., 4S, CARE, WOSCOPS, LIPID or CARDS), the relative risk reduction for a cardiovascular event was only up to 37% with limited therapeutic utility available to address the remaining cardiovascular excess risk in patients with dyslipidemia. Therefore, an unmet need exists for further lipid-lowering drugs that can be used in combination therapy. So far, however, most drugs developed for this purpose either have limited efficacy on atherosclerosis progression (e.g., ezetimibe; Kastelein et al. 2008 N. Engl. J. Med. 358:1431), were withdrawn from the market due to side effects (e.g., systemic niacin/laropiprant; HSP2-THRIVE Collaborative Group 2013, Eur. Heart J. 34:1279) or are may even accelerate atherosclerosis (e.g., torcetrapib; Barter et al. 2007, N. Engl. J. Med. 357:2109). Non-alcoholic fatty liver disease (NAFLD) and non-alcoholic steatohepatitis (NASH) regularly accompany dyslipidemia. However, the occurrence and severity of NAFLD/NASH as an indication is often independent from the severity of dyslipidemia. NAFLD has become a leading cause for liver cirrhoses and hence liver transplantation and hepatocellular carcinoma. At present, no prescription drug carries the indication of specifically treating NAFLD/NASH.

Therefore, there is a large unmet need for pharmaceuticals that (1) deliver benefits to human lipid metabolism independent and additive to statin therapy, (2) have low production costs and (3) have a favorable side effect profile. Most drugs that are used in this field (e.g., statins) have a dose limiting toxicity, which compromises the potential efficacy (a recent example is the withdrawal of cerivastatin).

Thresholds for unfavourable or abnormal or imbalanced lipid levels in the blood and/or plasma and/or serum are well known in the art [see, e.g., the current guidelines of the European Society of Cardiology and the European Atherosclerosis Society (2011, Eur. Heart J. 32:1769) as well as the current guidelines of the American Association of Clinical Endocrinologists (Jellinger et al. 2012, Endocr. Pract. 18 Suppl. 1:1; Jellinger et al. 2012, Endocr. Pract. 18:269).

Nicotinic acid (niacin, vitamin B3) and/or nicotinamide (nicotinic acid amide) have been used for the therapy of niacin deficiency diseases (e.g., pellagra) for decades. It is also long known that nicotinic acid has a health-promoting effect on cholesterol lipoproteins in the blood [e.g., reduction of all apoB-containing particles, increase in high density lipoprotein (HDL) levels, increase in the HDL/low density lipoprotein (LDL) ratio and size of the LDL vesicles; Wahlberg et al. 1990, J. Intern. Med. 228:151; Seed et al. 1993, Atherosclerosis 101:61; Elam et al. 2000, JAMA 284:1263; McKenney et al. 2001, Am. J. Cardiol. 88:270; Villines et al. 2012, Curr. Atheroscler. Rep. 14:49]. Recently, nicotinic acid was identified as a protective nutrient in human NAFLD and showed efficacy in a murine NAFLD model (von Schönfels et al. 2014, Liver Int. doi: 10.1111/liv.12476).

The mechanism of action of nicotinic acid has been attributed to signalling via the G protein-coupled receptor GPR109A, which down-regulates lipolysis and the available amount of free fatty acids, and the direct inhibition of the hepatocyte diacylglycerol acyltransferase-2 (Villines et al. 2012, Curr. Atheroscler. Rep. 14:49). However, this concept has recently been challenged (Lauring et al. 2012, Sci. Transl. Med. 4:148ra115) and it does not explain that nicotinic acid raises HDL plasma levels significantly in many patient cohorts and indications, which is supposed to be a multifaceted process with diverse signalling events (Villines et al. 2012, Curr. Atheroscler. Rep. 14:49). In addition, the mechanisms of action of the effect of nicotinamide on blood lipids, especially the elevation of HDL in patients with renal disease, are unclear and under debate (Rennick et al. 2013, Pharmacotherapy 33:683).

Systemic application of nicotinic acid has long been used for the treatment of dyslipidemia in cardiovascular and metabolic diseases (Villines et al. 2012, Curr. Atheroscler. Rep. 14:49). Interestingly, several studies have found that nicotinamide can also significantly raise HDL levels in hemodialysis patients (Takahashi et al. 2004, Kidney Int. 65:1099; Cheng et al. 2008, Clin. J. Am. Soc. Nephrol.

3:1131; Shahbazian et al. 2011, Nefrologia 31:58). The therapeutic benefits of nicotinic acid and nicotinamide in end stage renal disease have recently been reviewed by Rennick et al. in 2013 (Pharmacotherapy 33:683). In contrast to nicotinic acid, nicotinamide with its much better side effect profile can easily be used without delayed- or controlled release formulations (Takahashi et al. 2004, Kidney Int. 65:1099; Cheng et al. 2008, Clin. J. Am. Soc. Nephrol. 3:1131; Shahbazian et al. 2011, Nefrologia 31:58). All the state-of-the-art formulations, however, aim for delivering the nicotinic acid and/or nicotinamide quantitatively into the blood and, thus, for systemic exposure.

NA and NAM are classified as nutrition supplements (European Commission EC regulation no. 1170/2009). The European Scientific Committee on Food has defined the tolerable upper intake level for NA in adults at 10 mg/d without anticipated side effects (SCF/CS/NUT/UPPLEV/39). However, in the pharmacological use, clinically relevant lipid regulation was only seen in systemic doses of 2,000 mg/d and above. At doses higher than 100-300 mg/d, side effects including flush, tachycardia, blood pressure dysregulation and diarrhea have to be anticipated (Carlson 2005, J. Intern. Med. 258:94; statement no. 018/2012 of the German Federal Institute for Risk Assessment). In order to smoothen systemic uptake and to avoid high peak concentrations resulting in side effects, NA has been preferably administered in delayed or extended release formulations (e.g., Niaspan®) or in combination with acetylsalicylic acid or laropiprant (e.g., Tredaptive®). Such NA formulations were also the major intellectual property resulting in proprietary drugs, as unformulated NA cannot be administered in sufficient quantities. However, these drugs were recently withdrawn from the European market due to their unfavourable risk-benefit ratio resulting from significant side effects, which were largely due to systemic availability and, in the case of Tredaptive®, to the additive laropriprant. In contrast to NA, NAM with its much better side effect profile can be used without delayed or controlled release formulations (Takahashi et al. 2004, Kidney Int. 65:1099; Cheng et al. 2008, Clin. J. Am. Soc. Nephrol. 3:1131; Shahbazian et al. 2011, Nefrologia 31:58). This is reflected by the recommended maximum nutritional doses of up to 900 mg/d for adults (SCF/CS/NUT/UPPLEV/39). However, rapid systemic uptake will not provide sufficient amounts of the drug to the lower small intestine (preferably the terminal ileum) and/or colon, and the NA/NAM effects on the microbiota therefore need to be maximised by a controlled release formulation.

Accordingly, the pharmacokinetics for diverse nicotinic acid formulations (e.g., the extended release formulation Niaspan®) or nicotinamide formulations (e.g., Nicobion® or Endur-Amide®) show quick and almost quantitative resorption and metabolisation of the drug substance in different cohorts of patients and healthy volunteers (Petley et al. 1995, Diabetes 44:152; Dragovic et al. 1995, Radiother. Oncol. 36:225; Stratford et al. 1996, Br. J. Cancer 74:16; Bernier et al. 1998, Radiother. Oncol. 48:123; Menon et al. 2007, Int. J. Clin. Pharmacol. Ther. 45:448; Reiche et al. 2011, Nephrol. Dial. Transplant. 26:276).

Baseline plasma levels for nicotinic acid are difficult to determine, because nicotinic acid undergoes extensive, rapid and saturable first-pass metabolism with at least two separate pathways (Reiche et al. 2011, Nephrol. Dial. Transplant. 26:276; Villines et al. 2012, Curr. Atheroscler. Rep. 14:49). After administration of extended-release nicotinic acid, plasma $C_{max}$ was 9.3 µg/mL in healthy volunteers after a dose of 2 g (Menon et al. 2007, Int. J. Clin. Pharmacol. Ther. 45:448) or 4.22 µg/mL in patients with chronic kidney disease after a dose of 1.5 g (Reiche et al. 2011, Nephrol. Dial. Transplant. 26:276). Baseline nicotinamide levels in healthy volunteers without nicotinamide supplementation have been measured in the range of 0.008-0.052 µg/mL in a cohort of 30 healthy volunteers (calibration study of a German reference laboratory: Medizinisches Labor Bremen, www.mlhb.de, 2002). A systematic pharmacokinetic comparison study in healthy human volunteers reported a plasma $C_{max}$ of 2.1 µg/mL (after a 500-mg dose) and 16.2 µg/mL (after a 2-g dose) for the sustained release nicotinamide formulation Endur-Amide® (Petley et al. 1995, Diabetes 44:152). In a high-dose trial with Nicobion® in radiotherapy, a 6-g dose even led to peak plasma concentrations of approximately 142 µg/mL (Bernier et al. 1998, Radiother. Oncol. 48:123). Due to hepatotoxicity concerns, such high doses are far beyond the scope of the present invention.

Interestingly, a beneficial modification of the intestinal microbiota, e.g., an increase in bifidobacteria, has been demonstrated to result in beneficial effects on blood lipid levels, particularly an increase in HDL (recently demonstrated and reviewed by Martinez et al. 2009, Appl. Environ. Microbiol. 75:4175; and Prakash et al. 2011, J. Biomed. Biotechnol. 2011:981214). Whereas the drug development of probiotics has largely failed proof of clinical efficacy in many indications such as IBD, there are some promising data—albeit with small effect sizes—on probiotics in dyslipidemia (e.g., Jones et al. 2012, Br. J. Nutr. 107:1505). However, probiotics will always be inferior to improving or normalising the whole microbiome. The inventors are convinced that understanding a patient's microbiome and modifying it gently by NA or NAM (or a combination of both) via the body's own signalling mechanisms will be a mainstay of future therapies for metabolic diseases in general and dyslipidemia in particular.

SUMMARY OF THE INVENTION

The object of the present invention is to provide new forms of treatments for the therapy and/or prophylaxis of, e.g., unfavourable or abnormal or imbalanced blood and/or plasma and/or serum lipid levels and/or metabolic diseases in humans and animals associated with unfavourable or abnormal changes or imbalances in the intestinal microbiota and/or an impaired interaction between the intestinal microbiota and intestines.

According to the invention, the above problem is solved by a pharmaceutical composition or treatment or prevention regimen, as defined in the claims and/or described in more detail herein, which comprises as active substance(s) nicotinic acid and/or nicotinamide and/or another compound described herein, which beneficially influences the intestinal microbiota and their interaction with the intestines, which, in turn, beneficially influences blood and/or plasma and/or serum lipid levels. In preferred embodiments, the nicotinic acid and/or nicotinamide are administered to locally influence the intestinal mucosa and the intestinal microbiota. For example, the active substance is formulated to be administered selectively, e.g., for at least partial topical efficacy, in the lower small intestine and/or colon, preferably in the terminal ileum and/or colon, where the intestinal microbiota to be modified are located. Other active substances which convert to nicotinic acid and/or nicotinamide in an animal body (e.g., a human body) are also contemplated by the present invention.

Based on these surprising findings, in the present invention, the pharmaceutical composition or treatment or prevention regimen, and in particular the term "pharmaceutical composition" has a broad meaning of a pharmaceutically and/or physiologically acceptable composition of the said active substance(s), which includes but is not limited to pharmaceutical formulations in the sense of medicaments (drugs) and which also includes nutraceuticals, dietary supplements, and in its broadest sense may even include food ingredients and foods. Therefore, depending on the dose of the active substance(s) and the formulation, a pharmaceutical composition according to the present invention includes, but is not limited to, formulations as medicaments, nutraceuticals, dietary supplements, food ingredients and/or foods. Preferred are medicaments, nutraceuticals, and dietary supplements. Particularly preferred are pharmaceutical compositions as medicaments or supplements.

Accordingly, pharmaceutical compositions are provided which contain nicotinic acid (niacin, vitamin B3) and/or nicotinamide. These two substances act individually or in combination with one another in a beneficial manner on the microbiota in the small intestine and/or large intestine. A combination may be present in the same or separate dosage forms, which may be administered simultaneously or sequentially. The composition is suitable for oral administration with controlled and/or delayed release of the active ingredient for specific local or topical efficacy in the lower small intestine and/or colon, preferably in the terminal ileum and/or colon. Exemplary conditions treated include therapy (using a medicament) and/or prophylaxis (e.g., using a medicament, dietary supplement, food ingredient or food) of lipid metabolism disorders, dyslipidemia, non-alcoholic fatty liver disease (NAFLD), non-alcoholic steatohepatitis (NASH), cardiovascular diseases like arteriosclerosis and atherosclerosis, metabolic syndrome, obesity, and therapy and/or prophylaxis of other diseases featuring abnormal blood and/or plasma and/or serum lipid levels which partly or entirely result from changes in the intestinal microbiota and/or an impaired interaction between intestinal microbiota and intestines.

The invention also includes methods of treating or preventing one or more of the diseases and conditions described herein with a pharmaceutical composition described herein. In addition, the invention provides the use of a pharmaceutical composition described herein in the manufacture of a medicament for treating or preventing one or more of the diseases and conditions described herein and of a dietary supplement, food ingredient or food for helping to prevent one or more of the diseases and/or conditions described herein.

DETAILED DESCRIPTION

Figure 1:
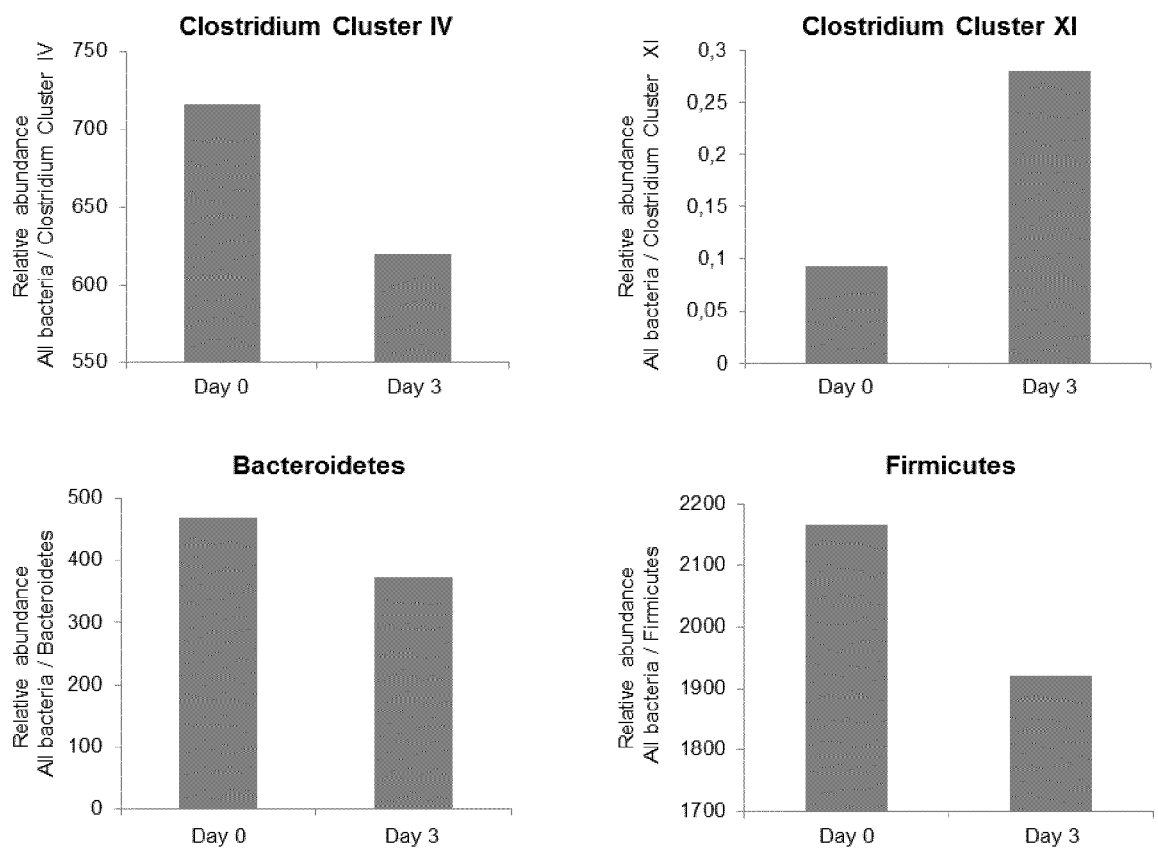
FIG. 1 shows the differential regulation of the relative abundance of some key groups of intestinal microbiota before (day 0) and after (day 3) treatment with controlled-release nicotinic acid (average of two healthy volunteers).

The core of the invention is a pharmaceutical composition or a treatment or prevention regimen comprising one, two or more active substance(s) selected from nicotinic acid; nicotinamide; a compound like, e.g., inositol hexanicotinate that converts in the body of an animal (e.g., a human body) into nicotinic acid or nicotinamide; nicotinamide adenine dinucleotide (NAD); nicotinamide adenine dinucleotide phosphate (NADP); an intermediate in the biosynthesis of NAD or NADP, for beneficially influencing (e.g., unfavourable or abnormal or imbalanced) blood and/or plasma and/or serum lipid levels by beneficially modifying the intestinal microbiota, wherein the pharmaceutical composition is designed for a controlled and/or delayed release so that it releases (e.g., partially releases, selectively releases) for at least partial topical efficacy in the lower small intestine, preferably in the terminal ileum, and/or in the colon.

Thus, in one embodiment, the invention provides for a pharmaceutical composition comprising an active substance selected from nicotinic acid; nicotinamide; a compound like, e.g., inositol hexanicotinate that converts in the body of an animal or human into nicotinic acid or nicotinamide; nicotinamide adenine dinucleotide (NAD); nicotinamide adenine dinucleotide phosphate (NADP); an intermediate in the biosynthesis of NAD or NADP; or a combination thereof for beneficially influencing (e.g., unfavourable or abnormal or imbalanced) blood and/or plasma and/or serum lipid levels by beneficially modifying the intestinal microbiota, wherein the pharmaceutical composition releases the active substance for at least partial topical efficacy in the lower small intestine, preferably in the terminal ileum, and/or the colon.

Accordingly, the pharmaceutical composition is comprising an active substance selected from nicotinic acid, nicotinamide, or a combination thereof for beneficially influencing the intestinal microbiota, wherein the pharmaceutical composition releases the active substance for topical efficacy in the lower small intestine, preferably in the terminal ileum, and/or the colon.

A combination may be present in the same or separate dosage forms, which may be administered simultaneously or sequentially.

In another embodiment the invention is directed to the use of the pharmaceutical composition, for beneficially influencing (e.g., unfavourable or abnormal or imbalanced) blood and/or plasma and/or serum lipid levels by beneficially modifying the intestinal microbiota.

As used herein, the "lower small intestine" is the second half of the small intestine and the "terminal ileum" is the second half of the ileum.

As used herein, the term "topical efficacy" refers to a topical effect, in the pharmacodynamic sense, and thus refers to a local, rather than systemic, target for a medication. Accordingly, local efficacy means a local therapy and/or prophylaxis of an active substance specifically or selectively to a location where, for example, the medication or dietary supplement or food ingredient shall deliver its direct therapeutic and/or prophylactic effect and does not or only to a low degree enter the circulatory system, e.g., thereby not causing any or only a low systemic action. In this regard, the topical efficacy of the present invention is also contrasted with enteral (in the digestive tract) and intravascular/intravenous (injected into the circulatory system) administrations. In comparison to compositions aiming at high systemic availability, the topical efficacy of compositions may also be characterized by longer latency times until systemic levels of the active substance(s) increase. Such latency times for topical release can be correlated with intestinal transit times known in the art (see, e.g., Davis et al. 1986, Gut 27:886; Evans et al. 1988, Gut 29:1035; Kararli 1995, Biopharm. Drug Dispos. 16:351; Sutton 2004, Adv. Drug Deliv. Rev. 56:1383). For example, after a variable time for gastric emptying (depending on the dosage form and feeding status and ranging from less than 1 hour to more than 10 hours), small intestinal transit times are rather constant with usually 3-4 hours across formulations and studies (Davis et al. 1986, Gut 27:886). Thus, an exemplary latency time in a fasted patient would be at least 2 hours, at which time a formulation reaches the lower small intestine and systemic levels may start to rise. Particularly, in the context of the present invention, topical efficacy preferably means that blood and/or plasma and/or serum levels of the active substance and/or metabolites thereof do not exceed levels which are two orders (preferably one order) of magnitude higher than the levels measured in the same person before dosing, while significantly and beneficially influencing at least one lipid parameter as defined in the current guidelines of the European Society of Cardiology and/or the European Atherosclerosis Society (2011, Eur. Heart J. 32:1769) and/or in the current guidelines of the American Association of Clinical Endocrinologists (Jellinger et al. 2012, Endocr. Pract. 18 Suppl. 1:1; Jellinger et al. 2012, Endocr. Pract. 18:269).

Alternatively or additionally, topical efficacy can be expressed in terms of a reduction of the blood and/or plasma and/or serum levels of at least 50%, 60%, 70%, 80%, 90% or even 95% or more relative to the same amount of active substance administered purely (without a formulation) in the same way and under the same conditions.

Topical efficacy is achieved in particular by the pharmaceutical formulations of the active substances as described herein.

Thus, preferred according to the invention is a pharmaceutical composition for oral administration with controlled and/or delayed release of the active ingredients for specific local efficacy in the lower small intestine, preferably in the terminal ileum, and/or the colon. In a more preferred variant, the pharmaceutical composition is formulated for oral administration with delayed release of the active ingredients for specific local efficacy in the lower small intestine, preferably in the terminal ileum, and/or the colon. In another more preferred variant, the pharmaceutical composition is formulated for oral administration with controlled release of the active ingredients for specific local efficacy in the lower small intestine, preferably in the terminal ileum, and/or the colon. Even more preferred according to the invention is that the pharmaceutical composition is comprising nicotinamide.

The inventors have previously demonstrated that nicotinamide has a surprising anti-inflammatory effect by influencing the intestinal microbiota (the entirety of all microorganisms in the intestines, in particular the bacteria) (PCT/EP2013/062363). The mechanism behind this surprising effect has subsequently been shown to involve nicotinamide-induced changes in the secretion pattern of antimicrobial peptides in the intestines, which supports the maintenance and/or regeneration of the normal, healthy intestinal microbiota (Hashimoto et al. 2012, Nature 487:477).

Thus, as used herein, "beneficially influencing the intestinal microbiota" refers to causing a change in the intestinal microbiota that has a beneficial impact on health, especially on one or more of the diseases and conditions described herein. For example, beneficial impacts are associated with reducing the number of pathogenic bacteria, reducing the ratio of pathogenic bacteria to beneficial bacteria, increasing the diversity of the microbiota, increasing the amount of beneficial bacteria, and partly or completely reverting pathological changes in the enterotype of the microbiota (e.g., enterotypes associated with *Bacteroides, Prevotella* and *Ruminococcus*).

In addition, the present invention also relates to using the intestinal microbiota in part and/or in their entirety (the microbiome) as a biomarkers to identify beneficial microbiota and/or detrimental microbiota, to support patient or subject selection for the treatments or preventions described herein, to personalise and adapt the pharmaceutical compositions and/or treatments and/or preventions described herein, and/or to determine end points and efficacy benchmarks for the pharmaceutical compositions and/or treatments and/or preventions described herein.

The present invention shows that, in surprising contrast to the state of the art described in the Background section, significant systemic exposure to nicotinic acid and/or nicotinamide is not necessary to beneficially influence blood and/or plasma and/or serum lipid levels.

As mentioned supra, e.g., in view of hepatotoxicity concerns and other side effects, high doses as used in the prior art formulations are beyond the scope of the present invention. Moreover, the formulations claimed herein aim at beneficially modifying blood and/or plasma and/or serum lipid levels (at least partly) indirectly by modifying the gut microbiota and their interaction with the intestines, using a controlled release and/or delayed release formulation of nicotinic acid and/or nicotinamide or a compound like inositol hexanicotinate that converts in the body of an animal or human into nicotinic acid or nicotinamide; nicotinamide adenine dinucleotide (NAD); nicotinamide adenine dinucleotide phosphate (NADP); an intermediate in the biosynthesis of NAD or NADP; or a combination thereof with no or low systemic exposure.

As used herein, the term "systemic exposure" is defined such that blood and/or plasma and/or serum levels of the active substance and/or metabolites exceed levels which are two orders of magnitude higher than the levels measured in the same person before dosing. Accordingly, a low systemic exposure is defined such that blood and/or plasma and/or serum levels of the active substance and/or metabolites do not exceed levels which are two orders of magnitude higher than the levels measured in the same person before dosing. Thus, in contrast to the prior art, the present invention is designed for a topical efficacy by means of beneficially modifying blood and/or plasma and/or serum lipid levels indirectly by modifying the gut microbiota and their interaction with the intestines, e.g., locally in the lower small intestine, preferably in the terminal ileum, and/or in the colon, while particularly showing no or low systemic exposure.

Similar to the situation with the anti-inflammatory topical effects of nicotinic acid and nicotinamide, a main effect of these substances is to beneficially influence the intestinal microbiota and the interaction between the intestines and the microbiota, which, in turn, leads to a beneficial effect on blood and/or plasma and/or serum lipid levels. Noteworthy, the topical efficacy for beneficially influencing (e.g., unfavourable or abnormal or imbalanced) blood and/or plasma and/or serum lipid levels by beneficially modifying the intestinal microbiota as described herein is independent from the previously found anti-inflammatory topical effect, and is recognized for the first time by the present invention. Hence, the invention particularly shows the said topical efficacy also in treatments for the therapy and/or prophylaxis of, e.g., unfavourable or abnormal or imbalanced blood and/or plasma and/or serum lipid levels and/or metabolic diseases in humans and animals, in which a large-scale tissue inflammation (e.g., like in IBD) is not necessarily the dominant or only disease-driving mechanism. Accordingly, the invention is also suitable in the treatment and/or prophylaxis in patients that do not have major and/or relevant signs and/or symptoms of an intestinal inflammation.

Thus, as used herein, a "beneficial effect" on blood and/or plasma and/or serum lipid levels refers to changing the blood and/or plasma and/or serum levels of one or more blood lipids from a state of dyslipidemia partially or fully towards the reference levels observed in healthy control individuals, which are matched to the diseased individuals in terms of, e.g., age, sex, body weight, medication, etc. Such beneficial effects are preferably an increase in HDL if HDL levels are below the reference levels, a decrease in LDL if LDL levels are above the reference levels, a decrease in triglycerides if triglyceride levels are above the reference levels, and/or a decrease in total cholesterol if total cholesterol levels are above the reference levels.

Therapeutic intervention by establishment or re-establishment of a normal gut microbiota or by supplementation of beneficial bacteria has been shown to be efficacious in diverse disease models and in the respective human diseases. For example, Olszak et al. (Science 2012, 336:489) recently demonstrated that the pathological accumulation of invariant natural killer T cells in diseased organs in germ-free murine models of IBD or asthma can be prevented by colonising neonate mice with normal microbiota. In different diseases, studies have demonstrated beneficial effects of certain pre-, pro- or synbiotics. In IBD, some probiotics like VSL#3 (a mixture of *Bifidobacterium breve, Bifidobacterium longum, Bifidobacterium infantis, Lactobacillus acidophilus, Lactobacillus plantarum, Lactobacillus paracasei, Lactobacillus delbrueckii* ssp. *bulgaricus* and *Streptococcus thermophilus*) have been successfully used in a limited number of clinical studies. However, the drug development of probiotics in IBD and many other indications has largely failed proof of clinical efficacy. There are some promising data—albeit with small effect sizes—on probiotics in dyslipidemia (e.g., Jones et al. 2012, Br. J. Nutr. 107:1505), and lactobacilli can reduce blood cholesterol levels in obesity, but the mechanism is still not completely clear (reviewed by Caesar et al. 2010, J. Intern. Med. 268:320).

It appears that the supplementation of at least several strains of bacteria is usually requisite to provide significant therapeutic benefit. A recent example of spectacular efficacy of a complex bacterial intervention is the successful use of stool transplants against *Clostridium difficile* (van Nood et al. 2013, New Engl. J. Med. 368:407). However, the present invention uses a more subtle approach than a complete microbial ecosystem transplantation by employing the intestine's own signalling mechanisms to beneficially influence and, ideally, normalise the endogenous and, thus, endemic gut microbiota.

The inventive, specific, topical use of nicotinic acid and/or nicotinamide (and related active substances) for locally influencing the intestinal mucosa and the intestinal microbiota, and the direct therapy of their interactions (or, e.g., the prophylaxis) resulting in beneficial lipid level changes result from the insights described herein into the formerly unknown and unexpected role of these compounds. This use significantly differs from conventional uses of the active substances, where these substances are absorbed and are supposed to act systemically. The main advantages of the present invention therefore are to avoid unnecessary systemic exposure, to reduce doses by delivering lower amounts of active substance(s) to the actual sites of efficacy and, consequently, to reduce or avoid systemic side effects by reducing or avoiding systemic uptake of the active substance(s).

On account of their beneficial effect on blood lipids by modifying, e.g., beneficially influencing, the intestinal microbiota, nicotinic acid and/or nicotinamide (and the other compounds described herein) are thus suitable as active substances for treating diseases caused or accompanied by, e.g., unfavourable or abnormal changes or imbalances in blood and/or plasma and/or serum lipid levels. In addition, they are suitable to prevent or to help preventing such diseases and/or conditions in a prophylactic setting as a medicament or dietary supplement or food ingredient, respectively.

Particular conditions include the therapy and/or prophylaxis of a disease and/or syndrome associated with and/or accompanied by unfavourable or abnormal or imbalanced blood and/or plasma and/or serum lipid levels, and/or such disease being selected from the group consisting of lipid metabolism disorders, dyslipidemia, NAFLD (non-alcoholic fatty liver disease), NASH (non-alcoholic steatohepatitis), preferably NAFLD and/or NASH by decreasing the liver fat content and/or beneficially influencing blood and/or plasma and/or serum lipid levels, cardiovascular diseases like arteriosclerosis and atherosclerosis, metabolic syndrome, obesity, and therapy and/or prophylaxis of other diseases featuring, e.g., unfavourable or abnormal or imbalanced blood and/or plasma and/or serum lipid levels which partly or entirely result from, e.g., unfavourable or abnormal changes or imbalances in the intestinal microbiota and/or an impaired interaction between intestinal microbiota and intestines.

Dyslipidemias can be hypolipidemias (e.g., if HDL levels are too low) or hyperlipidemias (e.g., if LDL levels are too high) or a combination of hypo- and hyperlipidemias of two or more lipids or lipoproteins in the blood and/or plasma and/or serum. The lipid metabolism disorders and dyslipidemias described herein include genetic and non-genetic forms of such conditions or diseases or disorders. A genetical predisposition includes, but is not limited to, risk genotypes in the SLCO1B1, ABCG2 or ABCB1 genes. Dyslipidemia can be accompanied by high Lp (a) levels and/or alterations in homocysteine levels. The patients described herein include, but are not limited to, patients with statin intolerance.

The compositions of the present invention are particularly preferred for use in the following three indications: (1) general dyslipidemia, especially as an additive to statins (e.g., to increase HDL, which is not sufficiently provided by statins), (2) dyslipidemia in patients with high Lp (a) and statin intolerance (including, but not limited to, patients with SLCO1B1, ABCG2 and/or ABCB1 risk genotypes) and (3) NAFLD (non-alcoholic fatty liver disease) and/or NASH (non-alcoholic steatohepatitis), preferably the NAFLD and/or NASH by decreasing the liver fat content and/or beneficially influencing blood and/or plasma and/or serum lipid levels. In addition, in one embodiment, the compositions of the present invention are particularly preferred for use as dietary supplements for subjects with a dyslipidemia that does not yet require medical treatment, but is a risk factor for developing one or more of the above diseases.

In this regard, the invention is preferably directed to a pharmaceutical composition for use in patients or subjects with unfavourable or abnormal or imbalanced blood and/or plasma and/or serum lipid levels for beneficially influencing blood and/or plasma and/or serum lipid levels and/or in one or more therapies or prophylaxes selected from the group consisting of:
a) the therapy and/or prophylaxis of lipid metabolism disorders,
b) the therapy and/or prophylaxis of dyslipidemia,
c) the therapy and/or prophylaxis of non-alcoholic fatty liver disease (NAFLD), preferably by decreasing the liver fat content and/or beneficially influencing blood and/or plasma and/or serum lipid levels,
d) the therapy and/or prophylaxis of non-alcoholic steatohepatitis (NASH), preferably by decreasing the liver fat content and/or beneficially influencing blood and/or plasma and/or serum lipid levels,
e) the therapy and/or prophylaxis of cardiovascular diseases,
f) the therapy and/or prophylaxis of arteriosclerosis,
g) the therapy and/or prophylaxis of atherosclerosis,
h) the therapy and/or prophylaxis of the metabolic syndrome,
i) the therapy and/or prophylaxis of obesity,
j) the therapy and/or prophylaxis of other diseases featuring unfavourable or abnormal or imbalanced blood and/or plasma and/or serum lipid levels which partly or entirely result from unfavourable or abnormal changes or imbalances in the intestinal microbiota and/or an impaired interaction between intestinal microbiota and intestines.

A particular embodiment of this pharmaceutical composition is for increasing HDL blood levels and/or for use in one or more selected from the group consisting of lipid metabolism disorders, dyslipidemia, non-alcoholic fatty liver disease (NAFLD), non-alcoholic steatohepatitis (NASH), the NAFLD and/or NASH preferably by decreasing the liver fat content and/or beneficially influencing blood and/or plasma and/or serum lipid levels.

Preferably, these active substances are used in a pharmacological formulation that protects the largest possible amount of active substance from being absorbed by the body, e.g., from being absorbed into the circulatory system, in the upper small intestine and rather effects a release (e.g., controlled release and/or delayed release) into the lower small intestine and/or colon, preferably the terminal ileum and/or colon, where the intestinal microbiota to be modified are located (e.g., the active substance is selectively released in the lower small intestine and/or colon, preferably in the terminal ileum and/or colon).

In particular, the active substances described herein are thus suitable for being used in medicaments or dietary supplements with topical release (e.g., controlled and/or delayed release) for the therapy and/or prophylaxis of a condition and/or a disease and/or a syndrome associated with and/or accompanied by unfavourable or abnormal or imbalanced blood and/or plasma and/or serum lipid levels, e.g., by increasing HDL blood levels, and for therapy and/or prophylaxis of other diseases featuring unfavourable or abnormal or imbalanced blood and/or plasma and/or serum lipid levels which partly or entirely result from unfavourable or abnormal changes or imbalances in the intestinal microbiota and/or an impaired interaction between intestinal microbiota and intestines.

The claimed substances are equally usable for the therapy and/or prophylaxis of diseases with similar genesis in both human and other mammals, in particular in domestic and useful animals. Examples of such animals are dogs, cats, horses, camels or cows without objective restriction.

Active substances, i.e., nicotinic acid and/or nicotinamide, may be used in any form available on the market, e.g., produced by Merck KgaA.

In addition to nicotinic acid and nicotinamide, other related compounds can be used in the invention described herein as active substances. For example, compounds that convert into one of these agents (e.g., by hydrolysis, metabolism) in the human or animal body are suitable, such as nicotinic acid esters. In addition, intermediates in the synthesis of nicotinamide adenine dinucleotide (NAD) or NAD phosphate (NADP), such as N-formylkynurenine, L-kynurenine, 3-hydroxy-L-kynurenine, 3-hydroxyanthranilate, 2-amino-3-carboxymuconate semialdehyde, quinolinate, and beta-nicotinate D-ribonucleotide, can be used. Further examples include NAD and NADP.

Pharmaceutical compositions which contain nicotinic acid and/or nicotinamide (or one of the other substances described above), can be administered orally with a retarded, e.g., controlled and/or delayed, active substance release and/or also via a rectal mode of application (e.g., enemas or suppositories). The site of delivery of the active substance is preferably the lower small intestine and/or the colon (more preferably the terminal ileum and/or the colon) for modifying the gut microbiota and their interaction with the intestines, and thus differs fundamentally from modes of applications which—e.g., state-of-the-art therapies of dyslipidemia using nicotinic acid—pursue maximal absorption and metabolism in the organism and, thus, a systemic effect. In addition, the mode of administration according to the invention and the dosage according to the invention minimise the probability for the occurrence of the well-known side effects of nicotinic acid and/or nicotinamide.

In this regard, the present invention also comprises combination preparations of the active substances of the present invention, such as a variable dose combination or a fixed dose combination of nicotinic acid and nicotinamide. The combination described herein may be present in the same or separate dosage forms, which may be administered simultaneously or sequentially.

In this regard, the present invention also comprises other combination preparations, such as combinations of nicotinic acid and/or nicotinamide with acetylsalicylic acid and/or prostaglandin D2 antagonists, such as laropiprant, which reduce the side effects typical of nicotinic acid; and combinations with statins. The composition and dosage of such combinations is known to a person skilled in the art.

As used herein, the term "variable dose combination" refers to a combination of two or more active substances in drugs or dietary supplements whereby each of these substances is applied in the form of a separate pharmaceutical composition, e.g., two single dosage forms, which separate pharmaceutical composition may be administered together by consecutive or subsequent administration regimen. For example, a pharmaceutical composition of nicotinic acid in any suitable dosage thereof may be administered together, consecutively or subsequently, with a separate pharmaceutical composition of nicotinamide in any suitable dosage thereof. Thus, variable dosages of one active substance, e.g., of nicotinic acid, may be combined with variable dosages of another active substance, e.g., of nicotinamide. These variable dose combinations may use conventionally available pharmaceutical compositions or may be also achieved by customized polypharmacy via compounding.

In contrast to a variable dose combination, a fixed-dose combination is a combination drug or dietary supplement which is a formulation including two or more active pharmaceutical ingredients, e.g., active substances, combined in a single dosage form, which is manufactured and distributed in certain respective fixed doses. A fixed-dose combination mostly refers to a mass-produced product having a predetermined combination of drugs or dietary supplements (active substances) and respective dosages (as opposed to customized polypharmacy via compounding).

Thus, the invention also pertains to embodiments of a pharmaceutical composition or the use thereof as described herein, wherein the pharmaceutical composition is a controlled and/or delayed release formulation of nicotinic acid or nicotinamide alone, or a variable dose combination or a fixed dose combination of a controlled and/or delayed release formulation of nicotinic acid with a controlled and/or delayed release formulation of nicotinamide. Preferably, the pharmaceutical composition is a fixed dose combination of the controlled and/or delayed release formulation of nicotinic acid with the controlled and/or delayed release formulation of nicotinamide. Controlled release formulations are preferred.

If combinations of nicotinic acid and nicotinamide are used according to the invention, they are preferably applied in a specific ratio by weight in the range of from 1:1 to 1:1000, in particular of from 1:3 to 1:300, preferably of from 1:10 to 1:100.

The total dosage of nicotinic acid and/or nicotinamide used according to the invention can be in the range of from 1 to 5000 mg, which may be administered as an individual dosage or as multiple dosages and/or a once, twice or more often daily dosage. Suitable total dosage ranges of nicotinic acid and/or nicotinamide comprise of from 50 to 5000 mg, preferably of from 100 to 5000 mg. The preferred total dosage of nicotinic acid and/or nicotinamide according to the invention is in the range of from 50 to 4000 mg each, more preferably in the range of from 100 to 4000 mg each.

As a non-limiting example, a high dose formulation can comprise up to 5000 mg of nicotinic acid, nicotinamide and/or a combination thereof. For example, but not limited to, a fixed-dose high dose formulation can comprise a total of nicotinic acid and nicotinamide in the range of 3000-5000 mg, preferably in the range of 3500-5000 mg. A suitable high dose formulation is in the range of 3750-4250 mg, e.g., 4000 mg. For high dosage formulation, care should be taken that the controlled and/or delayed release formulation is composed such as not to effect an undesired high systemic exposure.

As a non-limiting example, a low dose formulation can comprise up to 1000 mg, e.g., 500-600 mg of nicotinic acid, nicotinamide and/or a combination thereof.

As a non-limiting example, a standard dose formulation can comprise up to 3000 mg, and preferably is in a range of from 1000-2500 mg, more preferably in the range of from 2000-2500 mg, of nicotinic acid, nicotinamide and/or a combination thereof.

A non-limiting particular example of a fixed-dose high dose formulation comprises a combination of 1000 mg nicotinic acid (NA) and 3000 mg nicotinamide (NAM).

A non-limiting particular example of a fixed-dose standard dose formulation comprises a combination of 250 mg nicotinic acid and 2000 mg nicotinamide.

A non-limiting particular example of a fixed-dose low dose formulation comprises a combination of 50 mg nicotinic acid and 500 mg nicotinamide.

Such pharmaceutical compositions of the invention may, for example, be administered as a granulate, preferably a micro-granulate, if suitable in a capsule or sachet, and preferably in a sachet.

It is preferred that nicotinic acid and/or nicotinamide is formulated in the form of granules, preferably micro-granules. These granules, e.g., the micro-granules, can be used for single dosage forms or for variable dose combinations or fixed dose combinations. If nicotinic acid and/or nicotinamide in the form of granules, preferably micro-granules, are used in combination with other active substances as described herein, e.g., in combination with statins, these active substances may be used in form of any single pharmaceutical composition, as well as a variable dose combination or a fixed dose combination. Preferably, such other active substances, e.g. statins, may then be also used in the form of granules or micro-granules. Granules, preferably micro-granules, may be compressed into tablets, or filled into capsules or sachets, or used as such, as appropriate.

In order to produce orally administered formulations of an active substance (e.g., tablets, dragees, capsules, sachets, etc.) having a beneficial and/or modifying effect on the intestinal microbiota in the lower small intestine and/or in the colon, preferably in the terminal ileum and/or in the colon, it is thus advantageous and innovative to use controlled and/or delayed modes of release. In contrast to conventional (in some cases also delayed, but systemic) modes of release for optimum supplementation certain embodiments of the present invention, e.g., in the case of using nicotinic acid for treating dyslipidemia, (at least) partially or (even) substantially avoid an absorption in the stomach and in the upper portions of the small intestine.

In order to treat or prevent the diseases and/or unfavourable physiological conditions mentioned above, oral and/or rectal modes (e.g., as enema) of application are suitable. The oral application is preferred.

Thus, preferred according to the invention is a pharmaceutical composition for the oral administration with controlled and/or delayed active substance release for the therapy and/or prophylaxis of a disease and/or syndrome associated with and/or accompanied by unfavourable or abnormal or imbalanced blood and/or plasma and/or serum lipid levels, and/or such disease being selected from the group consisting of lipid metabolism disorders, dyslipidemia, non-alcoholic fatty liver disease (NAFLD), non-alcoholic steatohepatitis (NASH), preferably NAFLD and/or NASH by decreasing the liver fat content and/or beneficially influencing blood and/or plasma and/or serum lipid levels, cardiovascular diseases, arteriosclerosis, atherosclerosis, metabolic syndrome, obesity, and/or for the therapy and/or prophylaxis of other diseases and/or medical conditions featuring unfavourable or abnormal or imbalanced blood and/or plasma and/or serum lipid levels which partly or entirely result from unfavourable or abnormal changes or imbalances in the intestinal microbiota and/or an impaired interaction between intestinal microbiota and intestines.

For oral administration, particular dosage forms that control and/or delay the release of the active substance due to special galenics (so-called controlled release, slow release or delayed release forms) are particularly suitable. Such dosage forms may be simple tablets and also coated tablets, e.g., film tablets or dragees. The tablets are usually round or biconvex. Oblong tablet forms, which allow the tablet to be separated, are also possible. In addition, granules, spheroids, pellets or microcapsules are possible, which are filled in sachets or capsules, where appropriate.

The term "delayed release" relates preferably to a pharmaceutical formulation that releases the active ingredients after a period of delay. In certain embodiments, the delay is sufficient for at least a portion of the active substances in a formulation to release in the lower small intestine (e.g., in the terminal ileum) and/or colon.

The term "controlled release" refers preferably to a pharmaceutical formulation or component thereof that releases, or delivers, one or more active ingredients over a prolonged period of time (time-dependent release) and/or under certain physiological conditions (e.g., pH-dependent release). In certain embodiments, the period of time or the release according to physiological conditions (e.g., pH) is sufficient for at least a portion of the active substances in a formulation to release in the lower small intestine (e.g., in the terminal ileum) and/or colon.

The retardation and/or delayed release and/or controlled release is advantageously achieved, e.g., by coatings which are resistant to gastric juice and dissolve depending on the pH, by means of microcellulose and/or multi matrix (MMX) technologies, by using different carrier matrices or a combination of these techniques. Examples include film coatings which contain acrylic and/or methacrylate polymers in various mixtures for controlled and/or delayed release. Additional examples include biodegradable polymers like natural or chemically modified pectins as polymer-drug conjugates, coatings and/or matrix agents for microbiota-dependent release (reviewed, e.g., by Vandamme et al. 2002, Carbohydrate Polymers 48:219). For example, the active substance(s) can be contained in a conventional matrix of microcrystalline cellulose or gelatin or with MMX technology, which is coated with a material, which provides the delayed release of the active substance(s). An active substance can be administered in large-volume capsules (e.g., gelatin capsules having a content of 0.68 ml), which are coated by means of known methods. Suitable coating agents are water-insoluble waxes, such as carnauba wax, and/or polymers, such as poly(meth)acrylates [e.g., the poly(meth) acrylate product portfolio with the trade name Eudragit®, in particular Eudragit® L 30 D-55 (an aqueous dispersion of anionic polymers with methacrylic acid as a functional group), Eudragit® L 100-55 (which contains an anionic copolymer based on methacrylic acid and ethyl acrylate), Eudragit® L 100 or L 12.5 or S 100 or S 12.5 (anionic copolymers based on methacrylic acid and methyl methacrylate), or Eudragit® FS 30 D (an aqueous dispersion of an anionic copolymer based on methyl acrylate, methyl methacrylate and methacrylic acid); Evonik Industries AG, Essen, Germany) and/or water-insoluble celluloses (e.g., methyl cellulose, ethyl cellulose). Where appropriate, water soluble polymers (e.g., polyvinylpyrrolidone), water-soluble celluloses (e.g., hydroxypropylmethyl cellulose or hydroxypropyl cellulose), emulsifiers and stabilisers (e.g., polysorbate 80), polyethylene glycol (PEG), lactose or mannitol can also be contained in the coating material.

For example, a combination of Eudragit® S and L compounds (e.g., Eudragit® L/S 100) effects a controlled release of the active substances according to the invention at pH>6.4, which occurs in the terminal ileum. Further uses of Eudragit® preparations and mixtures thereof (FS, L, S and R compounds) are also conceivable for the packaging of an active substance, and therefore a topical use in selected portions of the entire gastrointestinal tract can be achieved by controlled release at certain pH values. A systematic study of enteric targeting with hydroxypropyl methylcellulose (HPMC) capsules and more recently developed Eudragit® polymers was published by Cole et al. in 2002 (Int. J. Pharm. 231:83).

Non-limiting examples especially for the formulation of dietary supplements, but also food ingredients, according to the present invention have been described recently by Berg et al. (2012, J. Food Eng. 108:158) for highly water soluble substances. Thus, the active substances according to the present invention can, e.g., be formulated as spray-dried maltodextrin-pectin microcapsules and shellac-coated granulates.

The pharmaceutical composition, e.g., a formulation of medicaments or a formulation of dietary supplements, can also contain further pharmaceutical excipient substances, such as binders, fillers, glidants, lubricants and flow regulating agents. The compounds according to the invention can be formulated, where appropriate, together with further active substances and with excipients conventional in pharmaceutical compositions, e.g., talcum, gum arabic, lactose, starch, magnesium stearate, cocoa butter, aqueous and non-aqueous carriers, lipid components of animal or vegetable origin, paraffin derivatives, glycols (in particular polyethylene glycol), various plasticizers, dispersants, emulsifiers and/or preservatives.

Another embodiment of the pharmaceutical composition according to the invention is for the rectal administration in the colon for the therapy and/or prophylaxis of diseases featuring unfavourable or abnormal or imbalanced blood and/or plasma and/or serum lipid levels which partly or entirely result from unfavourable or abnormal changes or imbalances in the intestinal microbiota and/or an impaired interaction between intestinal microbiota and intestines. This pharmaceutical composition is, e.g., formulated for rectal administration in the colon, wherein the therapy and/or prophylaxis is for a disease and/or syndrome associated with and/or accompanied by unfavourable or abnormal or imbalanced blood and/or plasma and/or serum lipid levels, and/or such disease being selected from the group consisting of lipid metabolism disorders, dyslipidemia, non-alcoholic fatty liver disease (NAFLD), non-alcoholic steatohepatitis (NASH), preferably NAFLD and/or NASH by decreasing the liver fat content and/or beneficially influencing blood and/or plasma and/or serum lipid levels, cardiovascular diseases, arteriosclerosis, atherosclerosis, metabolic syndrome, obesity, and/or for the therapy and/or prophylaxis of other diseases and/or medical conditions featuring unfavourable or abnormal or imbalanced blood and/or plasma and/or serum lipid levels which partly or entirely result from unfavourable or abnormal changes or imbalances in the intestinal microbiota and/or an impaired interaction between intestinal microbiota and intestines. The pharmaceutical composition, which with the rectal application is performed, is for the local modification of the microbiota in the colon.

In order to produce enemas or suppositories for rectal application, preparations of an active substance can be dissolved in a suitable solvent and be further processed into enemas or suppositories according to known pharmaceutical methods.

The active substance content in the finished dosage form is as described above. In a non-limiting example of a formulation, the active substance content for one or more substances may be of from 1 to up to 3000 mg each, preferably of from 10 up to 2500 mg each, in the case of oral administration; the enemas and/or suppositories can contain an amount of 10 mg to 5000 mg of the active substance. Depending on the nature and severity of the disease or condition as well as individual patient or subject characteristics, the dosage forms are administered once or several times daily, or in another dosage regimen to be chosen by a physician in case of medicaments or, in the case of dietary supplements, defined by the package instructions.

The pharmaceutical composition according to the invention or the use thereof as described herein, including variable dose combinations and fixed dose combinations, particularly comprises embodiments wherein nicotinic acid and/or nicotinamide are formulated for beneficially influencing blood and/or plasma and/or serum lipid levels and/or for the use in one or more selected from the group consisting of:
a) the therapy and/or prophylaxis of lipid metabolism disorders,
b) the therapy and/or prophylaxis of dyslipidemia,
c) the therapy and/or prophylaxis of non-alcoholic fatty liver disease (NAFLD), preferably by decreasing the liver fat content and/or beneficially influencing blood and/or plasma and/or serum lipid levels,
d) the therapy and/or prophylaxis of non-alcoholic steatohepatitis (NASH), preferably by decreasing the liver fat content and/or beneficially influencing blood and/or plasma and/or serum lipid levels,
e) the therapy and/or prophylaxis of cardiovascular diseases,
f) the therapy and/or prophylaxis of arteriosclerosis,
g) the therapy and/or prophylaxis of atherosclerosis,
h) the therapy and/or prophylaxis of the metabolic syndrome,
i) the therapy and/or prophylaxis of obesity,
j) the therapy and/or prophylaxis of other diseases featuring unfavourable or abnormal or imbalanced blood and/or plasma and/or serum lipid levels which partly or entirely result from unfavourable or abnormal changes or imbalances in the intestinal microbiota and/or an impaired interaction between intestinal microbiota and intestines.

This pharmaceutical composition or the use thereof according to the invention particularly also comprises embodiments wherein nicotinic acid and/or nicotinamide, alone and/or in a variable dose combination or fixed dose combination thereof, are used in a variable dose combination or fixed dose combination with a statin, for example with a statin selected from the group consisting of atorvastatin, cerivastatin, fluvastatin, lovastatin, mevastatin, pitavastatin, pravastatin, rosuvastatin and simvastatin, preferably with simvastatin.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "prophylaxis" and "prevent" refer to delaying the onset of or reducing the likelihood of developing a disease or disorder or one or more symptoms thereof, as compared to an untreated control population.

A further aspect of the invention described herein is the efficient use of the claimed medicaments or dietary supplements on the basis of genetic and/or microbiological data and specific needs of the individuals to be treated. New insights into the genetic predisposition of individuals for all types of diseases (in particular also diseases where the interaction between intestinal microbiota and intestines is impaired) and into pharmacogenetics indicate that an evidence-based personalized medicine including genetic analyses of relevant risk genes and also of genes which code e.g., for cell surface receptors, transporter proteins, metabolism enzymes or signal transduction proteins, which interact with the medicament and/or its metabolites and/or its downstream effectors, can contribute information and improvements with respect to the type of use, the mode of application, the time(s) of use, the dose and/or the dosage regimen of the medicaments or dietary supplements described herein. Individuals who may benefit from this personalised treatment include those with disease-specific or non-specific changes in blood and/or plasma and/or serum lipids. This applies analogously to analyses of the intestinal microbiota, particularly when a stool sample indicates a change in the microbiota. The present invention thus also comprises the use of suitable genetic and/or microbiological test methods to identify individuals particularly susceptible to the medicaments or dietary supplements according to the invention and/or to adapt the use of the medicaments according to the invention to the individual circumstances. This also comprises expressly the use of different substances or their combinations (e.g., nicotinic acid and/or nicotinamide) in different modes of administration depending on the genetic and microbiological properties of the individual. For these purposes, it is possible to use laboratory tests and/or suitable test kits and also measuring methods, devices and/or kits to be employed by a physician, user and/or patient, e.g., to take stool samples or to analyze suitable parameters in the blood, urine or other body fluids.

EXEMPLIFICATION

There are variable possibilities to advantageously develop, and develop further, the teaching of the present invention. For this purpose, reference is made to the examples below which describe the invention in a representative way.

If not indicated otherwise, the meaning of "%" is "% by weight".

Example 1

Nicotinic acid is encapsulated in gelatin capsules and coated with a mixture of Eudragit® FS 30 D/L 30 D-55 polymers for release at pH≥6.4.

In a further embodiment of the present invention, nicotinamide is encapsulated in gelatin capsules and coated with a mixture of Eudragit® FS 30 D/L 30 D-55 polymers for release at pH≥6.4.

In a further embodiment of the present invention, a mixture of nicotinic acid and nicotinamide is encapsulated in gelatin capsules and coated with a mixture of Eudragit® FS 30 D/L 30 D-55 polymers for release at pH≥6.4.

In a different embodiment of the present invention, nicotinic acid is encapsulated in HPMC capsules and coated with a mixture of Eudragit® FS 30 D/L 30 D-55 polymers for release at pH≥6.4.

In a further embodiment of the present invention, nicotinamide is encapsulated in HPMC capsules and coated with a mixture of Eudragit® FS 30 D/L 30 D-55 polymers for release at pH≥6.4.

In a further embodiment of the present invention, a mixture of nicotinic acid and nicotinamide is encapsulated in HPMC capsules and coated with a mixture of Eudragit® FS 30 D/L 30 D-55 polymers for release at pH≥6.4.

Nicotinic acid is encapsulated in gelatin capsules and coated with a mixture of Eudragit® S100/L100 polymers for release at pH≥6.4.

In a further embodiment of the present invention, nicotinamide is encapsulated in gelatin capsules and coated with a mixture of Eudragit® S100/L100 polymers for release at pH 6.4.

In a further embodiment of the present invention, a mixture of nicotinic acid and nicotinamide is encapsulated in gelatin capsules and coated with a mixture of Eudragit® S100/L100 polymers for release at pH≥6.4.

In a different embodiment of the present invention, nicotinic acid is encapsulated in HPMC capsules and coated with a mixture of Eudragit® S100/L100 polymers for release at pH≥6.4.

In a further embodiment of the present invention, nicotinamide is encapsulated in HPMC capsules and coated with a mixture of Eudragit® S100/L100 polymers for release at pH 6.4.

In a further embodiment of the present invention, a mixture of nicotinic acid and nicotinamide is encapsulated in HPMC capsules and coated with a mixture of Eudragit® S100/L100 polymers for release at pH≥6.4.

In yet another embodiment of the present invention, nicotinic acid is formulated as a granulate of 25% nicotinic acid, 70% dibasic calcium phosphate and 5% Povidone K30, which is film-coated with ethylcellulose 7 for time-dependent release.

In a further embodiment of the present invention, nicotinamide is formulated as a granulate of 25% nicotinamide, 70% dibasic calcium phosphate and 5% Povidone K30, which is film-coated with ethylcellulose 7 for time-dependent release.

In a further embodiment of the present invention, a mixture of nicotinic acid and nicotinamide is formulated as a granulate of 25% mixture of nicotinic acid and nicotinamide, 70% dibasic calcium phosphate and 5% Povidone K30, which is film-coated with ethylcellulose 7 for time-dependent release.

In yet another embodiment of the present invention, nicotinic acid is formulated as a granulate of 95% nicotinic acid and 5% Povidone K30, which is film-coated with ethylcellulose 7 for time-dependent release.

In a further embodiment of the present invention, nicotinamide is formulated as a granulate of 95% nicotinamide and 5% Povidone K30, which is film-coated with ethylcellulose 7 for time-dependent release.

In a further embodiment of the present invention, a mixture of nicotinic acid and nicotinamide is formulated as a granulate of 95% mixture of nicotinic acid and nicotinamide and 5% Povidone K30, which is film-coated with ethylcellulose 7 for time-dependent release.

In yet another embodiment of the present invention, nicotinic acid is formulated as a granulate of 95% nicotinic acid and 5% Povidone K30, which is coated with Eudragit® FS 30 D/L 30 D-55 polymers for release at pH≥6.4.

In a further embodiment of the present invention, nicotinamide is formulated as a granulate of 95% nicotinamide and 5% Povidone K30, which is coated with Eudragit® FS 30 D/L 30 D-55 polymers for release at pH≥6.4.

In a further embodiment of the present invention, a mixture of nicotinamide and nicotinic acid is formulated as a granulate of 95% mixture of nicotinic acid and nicotinamide and 5% Povidone K30, which is coated with Eudragit® FS 30 D/L 30 D-55 polymers for release at pH≥6.4.

In yet another embodiment of the present invention, nicotinic acid is formulated as a granulate of 95% nicotinic acid and 5% Povidone K30, which is coated with Eudragit® S100/L100 polymers for release at pH≥6.4.

In a further embodiment of the present invention, nicotinamide is formulated as a granulate of 95% nicotinamide and 5% Povidone K30, which is coated with Eudragit® S110/L100 polymers for release at pH≥6.4.

In a further embodiment of the present invention, a mixture of nicotinamide and nicotinic acid is formulated as a granulate of 95% mixture of nicotinic acid and nicotinamide and 5% Povidone K30, which is coated with Eudragit® S100/L100 polymers for release at pH 6.4.

As non-limiting examples, from the above formulations, a fixed-dose high dose formulation comprising a combination of 1000 mg nicotinic acid (NA) and 3000 mg nicotinamide (NAM), a fixed-dose standard dose formulation comprising a combination of 250 mg nicotinic acid and 2000 mg nicotinamide as well as a fixed-dose low dose formulation comprising a combination of 50 mg nicotinic acid and 500 mg nicotinamide are prepared.

These formulations both alone and in combinations are administered to healthy human volunteers or to patients with dyslipidemia once or twice daily at doses of, e.g., 250 mg, 500 mg, 1 g, 1.5 g or 2 g for the single active substance formulations or at the above doses for the combination formulations. Whereas the measurable concentrations of nicotinic acid and/or nicotinamide in the blood are not significantly higher (e.g., two orders of magnitude) than baseline levels (in contrast to existing formulations aiming for systemic absorption, see Background), the composition of the gut microbiota of the healthy volunteers (less pronouncedly) and the patients with dyslipidemia (more pronouncedly) changes over time and, consequently, blood lipid levels improve or are optimised over time, partly or fully changing towards a microbiota composition and/or blood lipid levels resembling the situation in healthy subjects.

Example 2

Pure nicotinic acid (NA; Ph. Eur. grade, purchased from AppliChem, Darmstadt, Germany) without excipients was manually encapsulated in hard gelatin capsules (size 0, target content: 400 mg, average content: 391 mg nicotinic acid), subcoated with SheffCoat™ clear VLV and coated with a mixture of Eudragit® L100 and Eudragit® S100 polymers for release at pH=6.3, in order to release in the lower small intestine and achieve maximum nicotinic acid concentrations in the terminal ileum, one of the key sites for modulating the gut microbiota. As the coating was still in the development phase, for a pilot test and proof-of-principle, optimally coated capsules with perfectly closed capsule gaps were manually selected and tested in a self-experiment by two healthy male physicians (age: 34 and 36 years, respectively; dose: one capsule with approximately 400 mg controlled-release NA daily). The readout were levels of LDL, HDL, triglycerides and NA in the blood.

The results of this experiment are summarised in Table 1.

TABLE 1

| Person | Time | Nicotinic acid [µg/mL] | LDL cholesterol [mg/dL] | HDL cholesterol [mg/dL] | Triglycerides [mg/dL] |
|---|---|---|---|---|---|
| Volunteer 1 | Day 0 | 0.0353 | 143 | 47 | 88 |
|  | Day 3 | 0.0820 | 128 | 50 | 57 |
| Volunteer 2 | Day 0 | 0.0345 | 179 | 53 | 167 |
|  | Day 3 | 0.1060 | 165 | 57 | 85 |

The results in Table 1 demonstrate that NA serum levels rose only slightly compared with published reference serum levels (see Background). As systemic NA is only efficacious in high doses, published doses are a plasma $C_{max}$ of 9.3 µg/mL in healthy volunteers after a 2-g dose of extended-release nicotinic acid (Menon et al. 2007, Int. J. Clin. Pharmacol. Ther. 45:448) or 4.22 µg/mL in patients with chronic kidney disease after a dose of 1.5 g (Reiche et al. 2011, Nephrol. Dial. Transplant. 26:276). Extrapolating to lower doses from these values, a systemically available formulation of 400 mg NA would have been expected to result in serum levels of 1.13-1.86 µg/mL, which is more than one order of magnitude higher (factor 10.66 to 22.68, depending on the paired values) than the NA serum levels measured in Volunteer 1 or 2 after three days of controlled-release NA.

Importantly, all lipid parameters (LDL cholesterol, HDL cholesterol and triglycerides) tendentially or clearly changed in a beneficial manner even after a 3-day exposure, suggesting a high efficacy of the controlled-release NA formulation and a quick adaptation of the gut microbiota.

In order to investigate whether and how controlled-release NA had influenced the intestinal microbiota, stool samples of the two volunteers were compared before and after days of dosing with controlled-release NA.

Total genomic DNA from equal amounts of fecal sample was extracted using the PowerSoil® DNA Isolation Kit (MoBio, Carlsbad, Calif.). In brief, the fecal sample was transferred into Power bead tubes (provided with the kit) containing 60 µL of solution C1 and 20 µL of a 20 mg/mL solution of Proteinase K. Samples were kept at 50° C. for 2 h.

Mechanical homogenisation and bead beating (using a FastPrep FP120 instrument, Thermo Fisher Scientific, Langenselbold, Germany) was performed to enhance the bacterial lysis. Remaining steps were performed according to the manufacturer's instructions. The amount of DNA was measured using the Quant-iT PicoGreen dsDNA Assay Kit (Life Technologies/Invitrogen, Darmstadt, Germany).

Amplification and detection of bacterial groups were carried out in 384-well plates on an ABI Prism 7900 sequence detection system (Life Technologies/Applied Biosystems, Darmstadt, Germany), using 5 ng of DNA in a final volume of 10 µL (master mix, primers, probes and enzymes according to the manufacturer's protocol). Custom Taqman assays and kits were purchased from Life Technologies. Relative quantification was performed using total bacterial DNA as control.

The primers and probes used for quantification are provided in the following Table 2.

TABLE 2

| All bacteria | Bakt_341F | CCTACGGGNGGCWGCAG |
|---|---|---|
|  | Bakt-805-R | GGACTACHVGGGTWTCTAAT |
|  | BAC-516-Probe | TGCCAGCAGCCGCGGTAATAC |
| Clostridium cluster IV | Clept_Fd | GCACAAGCAGTGGAGT |
|  | Clept_Rev | CTTCCTCCGTTTTGTCAA |
|  | Clept_Probe | AGGGTTGCGCTCGTT |
| Clostridium cluster XI | Clust_XI_Fd | ACGCTACTTGAGGAGGA |
|  | Clust_XI_Rev | GAGCCGTAGCCTTTCACT |
|  | Probe_clust_XI | GTGCCAGCAGCCGCGGTAATACG |
| Bacteroidetes | Bac 32F | AACGCTAGCTACAGGCT-TAACA |
|  | BactR | ACGCTACTTGGCTGGTTCA |
|  | Bacteroidetes_346 probe | CAATATTCCT-CACTGCTGCCTC CCGTA |
| Firmicutes | 8F | AGAGTTTGATCCTGGCTCAG |
|  | 534R | ATTACCGCGGCTGCTGG |
|  | Firmicutes_probe | CTGATGGAGCAACGCCGCGT |

The results of the microbiota analysis are shown in FIG. 1 and demonstrate that nicotinic acid (like nicotinamide, see PCT/EP2013/062363 and Hashimoto et al. 2012, Nature 487:477) leads to drastic shifts in microbial communities if delivered locally to the lower small intestine and/or colon. The affected genera have previously been shown to be associated with different metabolic states in humans and animals. For example, a decrease in Firmicutes as observed in the present experiment (FIG. 1) has been associated with beneficial metabolic effects in obese mice (Everard et al. 2011, Diabetes 60:2775) and humans (Zhang et al. 2009, Proc. Natl. Acad. Sci. USA 106:2365).

In summary, these data support the therapeutic principle of the present invention, namely minimal systemic exposure and topical efficacy on the interaction between the gut microbiota and the intestines, which is in contrast to all teachings of the prior art.

Example 3

After the successful first test demonstrating only little systemic uptake with a test formulation (Example 2), a larger study was performed. As described in Example 2, optimally coated capsules with perfectly closed capsule gaps were manually selected and tested in a self-experiment by four physicians (three male, one female; see Table 3) with two capsules daily, each containing approximately 400 mg controlled-release nicotinic acid (NA). The readout were serum levels of HDL and LDL, liver fat content (fasting, without contrast medium; LOGIQ E9 ultrasound device; GE Healthcare) and body weight (for calculating the body mass index, BMI).

The results of this experiment are summarised in the following Table 3.

TABLE 3

| Volunteer No. | Sex | Age [y] | Height [cm] | Day | HDL [mg/dL] | LDL [mg/dL] | Liver fat | Weight [kg] | BMI |
|---|---|---|---|---|---|---|---|---|---|
| 1 | M | 51 | 182 | 0 | 42 | 131 | ++ | 102 | 30.79 |
|  |  |  |  | 11 | 47 | 122 | + | 99 | 29.89 |
|  |  |  |  | 12 | After crossover (1 tablet): flush with formication (face, torso), erythema, tachycardia. | | | | |
| 2 | F | 51 | 172 | 0 | 39 | 174 | +++ | 93 | 31.44 |
|  |  |  |  | 11 | 51 | 180 | ++ | 90 | 30.42 |
|  |  |  |  | 12 | After crossover (1 tablet): no flush. | | | | |
| 3 | M | 29 | 167 | 0 | 50 | 132 | – | 94 | 33.71 |
|  |  |  |  | 11 | 52 | 140 | – | 95 | 34.06 |
|  |  |  |  | 12 | After crossover (1 tablet): flush, erythema, diarrhea. | | | | |
| 4 | M | 34 | 180 | 0 | 51 | 164 | ++ | 72 | 22.22 |
|  |  |  |  | 11 | 54 | 132 | ++ | 70 | 21.60 |
|  |  |  |  | 12 | After crossover (1 tablet): flush with formication (face), erythema. | | | | |

The results in Table 3 demonstrate that during dosing with the formulation used in Examples 2 and 3, a beneficial effect on HDL serum levels was observed in 4/4 volunteers, a beneficial effect on LDL serum levels in 2/4 volunteers, a beneficial effect on liver fat in 2/3 volunteers and a reduction of BMI in 3/4 volunteers. In order to prove the pharmaceutical efficacy of the NA contained in the capsules, the volunteers swallowed one imperfectly coated capsule after the end of the 11-day study period, resulting in flushing and further side effects in 3/4 volunteers, whereas such symptoms were not observed during dosing with optimally coated capsules. These findings further support the teachings of the present invention, namely that beneficial effects of NA and/or nicotinamide on lipid metabolism can also be obtained with drug formulations minimising systemic exposure and that a significant part of these beneficial effects is due to the modification of the gut microbiota and their interaction with the intestines.

Example 4

In order to closely model the situation in human patients with inflammatory bowel diseases (IBD), a murine model for chronic colitis was tested for the first time under conditions of tryptophan reduction (25% of regular tryptophan and nicotinic acid content in the diet), but not complete starvation (as described in PCT/EP2013/062363). This model was of particular interest, because it is known that IBD lead to a reduction in total cholesterol and other blood lipid parameters, which is directly correlated with disease activity (Romanato et al. 2009, Aliment. Pharmacol. Ther. 29:298). The pharmaceutical compositions described herein and in PCT/EP2013/062363 have an anti-inflammatory effect and significant therapeutic efficacy in different colitis models, which is mediated by targeted modification of the intestinal microbiota (see PCT/EP2013/062363 and a co-pending application EP13197278.8, filed 13 Dec. 2013, entitled "Use of tryptophan as a biomarker for patient selection, dosing and therapy monitoring for pharmaceutical compositions targeting the intestinal microbiota in diseases featuring tryptophan deficiency", submitted by the same applicant as this application and which is entirely incorporated by reference). Therefore, investigating lipid levels in mice subjected to a chronic colitis under tryptophan (metabolite) reduction was an important point to support the mechanism of lipid level changes mediated by modification of the intestinal microbiota.

Due to species-specific differences in the gastrointestinal tract in terms of length, passage time and pH milieu, the controlled release formulations were adapted to the organism which was to be treated. Based on the parameters of the murine gastronintestinal tract (Koopman et al. 1978, Lab. Anim. 12:223; McConnell et al. 2008, J. Pharm. Pharmacol. 60:63), a murine-specific formulation was produced for this proof-of-concept study in mice.

Controlled release minitablets were produced with a powder mixed of 99% nicotinamide (NAM) and 1% of magnesium stearate (both from Caelo, Hilden, Germany) as lubricant. After blending, the powder was characterised in terms of powder flow (angle of repose; <35°) and size distribution (laser diffraction; main particle fraction: 100-200 μm) to ensure good powder flow. Minitablets were then produced in a rotary press and coated by a film of the water-insoluble polymer Kollidon SR 30 D (BASF, Ludwigshafen, Germany) to control NAM release by diffusion of NAM through the film. The coating formulation was as follows: Kollicoat SR 20 D (49.9%), glycerol monostearate 60 (0.743%), propylene glycol (0.743%), red iron oxide (0.4%), polysorbate 80 (0.314%), and water ad 100%.

The glycerol monostearate 60 (Caelo) was heated with half of the water to 80° C. and emulsified with an Ultraturrax (IKA, Staufen, Germany). Subsequently, the red iron oxide (Caelo) was added and dispersed for additional 5 min (first bin). The polysorbate 80 (Caelo), the propylene glycol (Caelo) and the polymer dispersions were combined in a second bin and stirred with a magnetic stirrer. The cool (<30° C.) emulsion from the first bin was combined with the polymer dispersion from the second bin, and the remaining water was added. The dispersion was stirred for 1 h before filtering (<500 μm). The minitablets were coated in a fluidised bed apparatus (Mycrolab, Hüttlin, Schopfheim, Germany) in a batch size of 50 g with a liquid feed rate of about 1 ml/min and a nebulizing pressure of 0.7 bar. Before spraying, the tablets were pre-heated by a volume flow of 8 $m^3$ at 45° C. During spraying, the volume flow was increased to 16 $m^3$ at 45° C. A product temperature of about 38° C. was observed. After spraying, the tablets were fluidised with 16 $m^3$ for additional 10 min at 45° C. for curing. In the final process step, the heating was switched off and the tablet bed was cooled to <30° C. to avoid sticking. The tablets were coated with 6.2±0.04 mg/$cm^2$. Drug release was determined in a paddle apparatus (DT6, Erweka, Heusenstamm, Germany) in according to the Ph. Eur. at 50 rpm. Phosphate buffer (pH 4) was used as dissolution medium because a slightly acid gastrointestinal fluid of about this pH is expected in mice (McConnell et al. 2008, J. Pharm. Pharmacol. 60: 63-70). The drug concentration was determined by UV absorption at 262 nm. The uncoated tablets showed an instantaneous drug release due to the minuscule size of the tablets and the high water solubility of nicotinamide. Using the Kollidon SR coating, the drug release was optimised to cover the target areas in the small intestine of the mice (at least 15 min lag time, constant drug release over 3 h).

The diet of pre-acclimatised male C57BL/6J mice (age 14 weeks) was switched to a custom-made diet with only 25% of the regular content of tryptophan or nicotinic acid or nicotinamide (termed Trp/Nia/NAM-low diet herein), which was produced by mixing a Trp/Nia/NAM-free diet (no tryptophan and 1% of a vitamin premixture without nicotinic acid) in a ratio of 3:1 with a normal diet containing 0.28% tryptophan and 1% of a vitamin premixture with nicotinic acid. Both custom diets were manufactured by Ssniff (Soest, Germany) and were supplied as a powder, which was used to prepare food pellets with either no minitablets (control) or NAM minitablets. The minitablets were homogeneously mixed with the Trp/Nia/NAM-low diet powder, pellets of approximately 2 cm length and 1 cm diameter were formed with a minimum amount of sterile water, frozen in single-use aliquots at −20° C. for storage and freshly thawed daily for feeding the mice. The mice received the changed Trp/Nia/NAM-low diet for 2 weeks before the first step of the colitis induction.

The treatment regimen was carried out with two groups of 5 mice each, which were treated as follows:
Group 1: Trp/Nia/NAM-low diet without minitablets (control).
Group 2: Controlled release NAM minitablets homogeneously dispersed in the diet (final dose: ca. 60 mg/kg bodyweight, based on a food intake of 2.5 g per mouse per day).

For chronic colitis induction, the mice were supplied with 2.5% (first cycle) and 3% (second cycle) of dextran sodium sulfate (DSS; molecular mass 40 kDa; TdB consultancy, Uppsala, Sweden) dissolved in the drinking water for 5 days followed by 5 days of regular drinking water. Surviving mice were sacrificed after the 5-day water period of the second DSS cycle (day 21). Survival was monitored daily.

Figure 2:
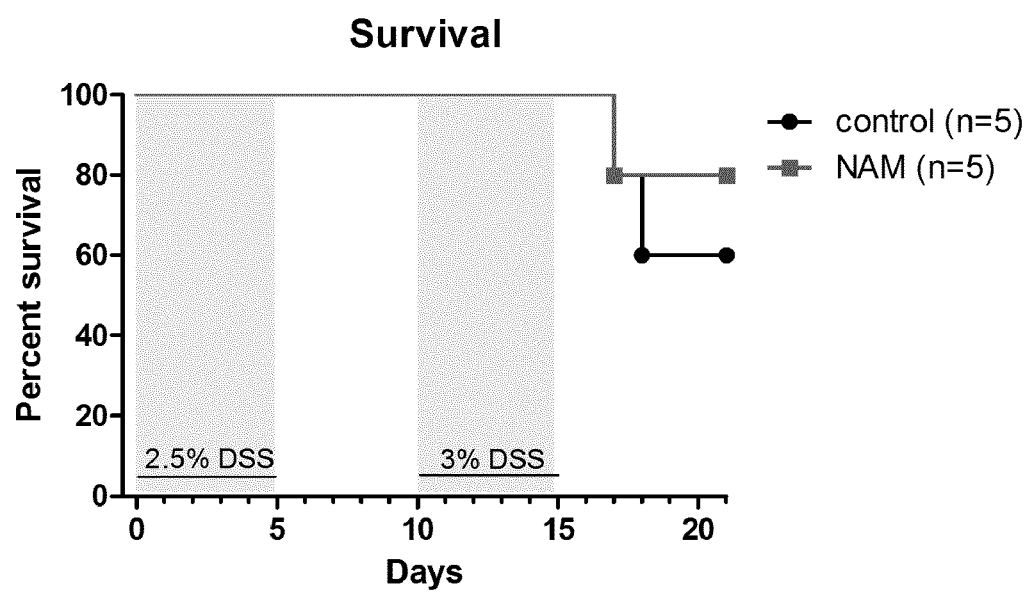
FIG. 2 shows that controlled-release nicotinamide minitablets (NAM; dose: approximately 60 mg/kg) conferred a survival benefit in chronic dextrane sodium sulfate (DSS) colitis in C57BL/6J mice (n=5 per group), which had been fed a diet with only 25% of the normal content of tryptophan, nicotinic acid and nicotinamide for 14 days prior to colitis induction. Surviving mice were terminated 5 days after the second cycle of DSS treatment.

Controlled-release NAM conferred a survival benefit (FIG. 2), which is of particular importance as the mice in this experiment were not completely starved of tryptophan, but rather featured a situation resembling the reduced availability of tryptophan and its metabolites in human patients, e.g., with IBD (see PCT/EP2013/062363 and a co-pending application EP13197278.8, filed 13 Dec. 2013, entitled "Use of tryptophan as a biomarker for patient selection, dosing and therapy monitoring for pharmaceutical compositions targeting the intestinal microbiota in diseases featuring tryptophan deficiency", submitted by the same applicant as this application and which is entirely incorporated by reference).

When mice had to be taken out of the study due to weight loss or immediately after termination of the surviving mice, serum was prepared and total cholesterol of the mice was analysed using standard techniques (Cobas® 8000 modular analyzer, Roche Diagnostics, Basel, Switzerland).

Figure 3:
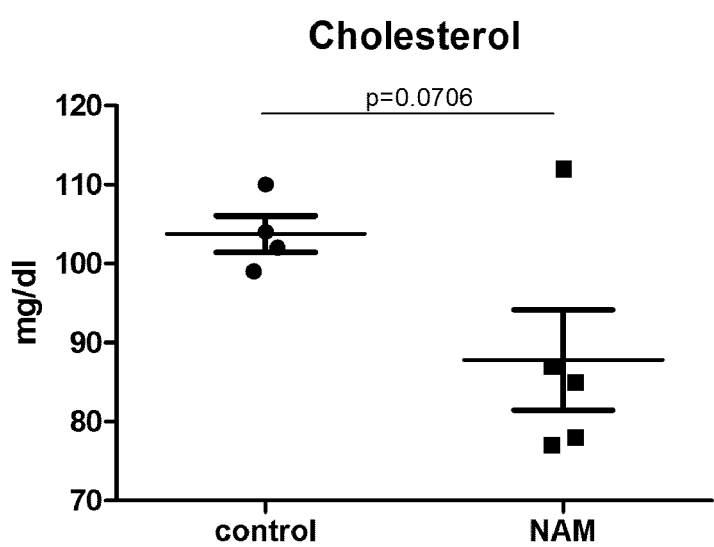
FIG. 3 shows that controlled-release nicotinamide minitablets (NAM; dose: approximately 60 mg/kg) reduced total cholesterol levels in C57BL/6J mice (n=5 per group), which had been fed a diet with only 25% of the normal content of tryptophan, nicotinic acid and nicotinamide for 14 days prior to being subjected to chronic dextrane sodium sulfate (DSS) colitis. Cholesterol levels are displayed as mean±standard deviation. One animal in the control group was not included in the cholesterol measurement, because it died without the possibility of immediate serum preparation.

Interestingly, despite the anti-inflammatory efficacy of the controlled-release NAM, which would be expected to raise cholesterol levels as a non-specific indicator for reduced colitis activity (Romanato et al. 2009, Aliment. Pharmacol. Ther. 29:298), total cholesterol in the mice was reduced (FIG. 3), which supports the notion that targeted modification of the intestinal microbiota by controlled-release formulations according to the present invention can directly and specifically reduce blood cholesterol.

Example 5

In order to extend the findings of von Schönfels et al. 2014 (Liver Int. doi: 10.1111/liv.12476) with NA in a chronic model of NAFLD, the effect of NAM was investigted in an acute murine model of NASH (Lee et al. 2012, Toxicol. Lett. 211:29). C57BL/6J mice (n=6; age: 12-13 weeks) were injected intraperitoneally with tunicamycin (TM; 2 µg/g body weight). After 48 h, the mice were sacrificed and liver tissue was collected for histological analysis of signs of NAFLD/NASH as described previously (Lee et al. 2012, Toxicol. Lett. 211:29). NAM was administered to three of the six mice in the drinking water from 2 days before the TM challenge until the end of the experiment. NAM was administered at 0.4 g/l, corresponding to approximately 60 mg/kg/d (assumptions from general averages: body weight of a mouse: 20 g; water intake: 3 mL/mouse/d; 3 mL with a concentration of 0.4 g/L contained 1.2 mg NAM, resulting in a dose of approximately 60 mg/kg/d).

Paraffin-embedded liver tissue sections (3 µm) from mice after TM challenge were subjected to hematoxylin/eosin staining and scored in a blinded manner. Hepatic steatosis, hepatocyte ballooning and inflammation were determined in a scoring system modified from Brunt 2001 (Semin. Liver Dis. 21:3). The stage scores were based on liver fibrosis. The 0-3 grading includes: 0, none; 1, mild; 2, moderate; and 3, severe.

Figure 4:
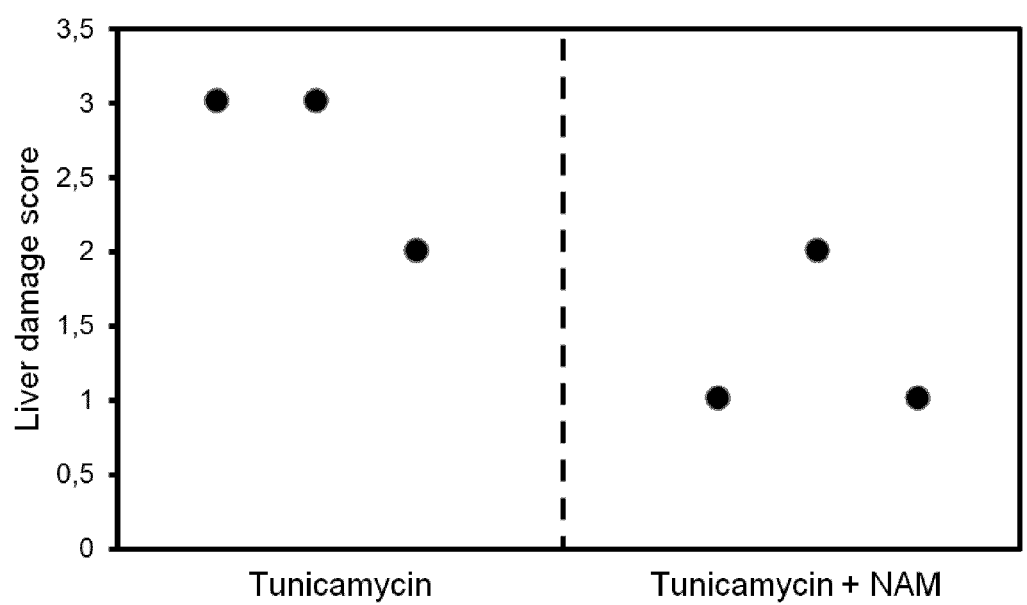
FIG. 4 shows the liver damage scores of 6 C57BL/6J mice challenged with tunicamycin (3 without NAM and 3 with 60 mg/kg NAM). NAM administration resulted in a moderate, but significant protection from tunicamycin-induced NAFLD/NASH. Each data point represents one mouse.

As shown in FIG. 4, mice receiving NAM showed a small, but significant reduction in TM-induced NAFLD-like liver damage.

Example 6

In a formulation development study to investigate the potential of nutritional formulations for the controlled release of NA or NAM, shellack-coated granule formulations based on Berg et al. (2012, J. Food Eng. 108:158) were tested.

Cellets (350 µm; IPC Process Center, Dresden, Germany) were coated with 0.5% NA (Sigma-Aldrich, Taufkirchen, Germany) using a Mini Glatt fluid bed coater (Glatt, Binzen, Germany) with a 0.5 mm nozzle at a spraying rate of 0.6 g/min. Atomizing air pressure was adjusted to 0.3-0.8 bar according to the weight gain of the granules. Fluid bed process air pressure was kept between 0.2 and 0.5 bar. The inlet air temperature was 45° C., and the outlet air temperature was 33-25° C. A subcoating containing 9% trehalose and 1% citric acid as suggested by Farag & Leopold 2011 (Eur. J. Pharm. Sci. 42:400) was applied onto the NA capsule. Subsequently, the granules were coated with 20% or 25% shellac (w/w) (SSB Aquagold 1243, 25% aqueous solution; Stroever-Schellack, Bremen, Germany). Any residual water in the coatings was removed by drying the microcapsules for 1 h at an inlet air temperature of 45° C.

Dissolution tests were conducted at 37° C. with 1 g granules in 300 ml of different dissolution media using a basket apparatus (Pharmatest DT 70, Hainburg, Germany) at 50 rpm. Dissolution media were simulated gastric fluid (SGF) pH 1.2 as described by USP, followed by simulated intestinal fluids (SIF) (i.e., phosphate buffer pH 6.8 or pH 7.4). The experiments were run for 2 h with SGF, followed by 4 h SIF pH 6.8 and 2 h SIF pH 7.4.

Drug release was monitored spectrophotometrically (Helios; Thermo Fisher Scientific, Waltham, Mass., USA) at 215 nm using a 1-mm Quartz cuvette. Samples were returned to the dissolution tester after each measurement.

Figure 5:
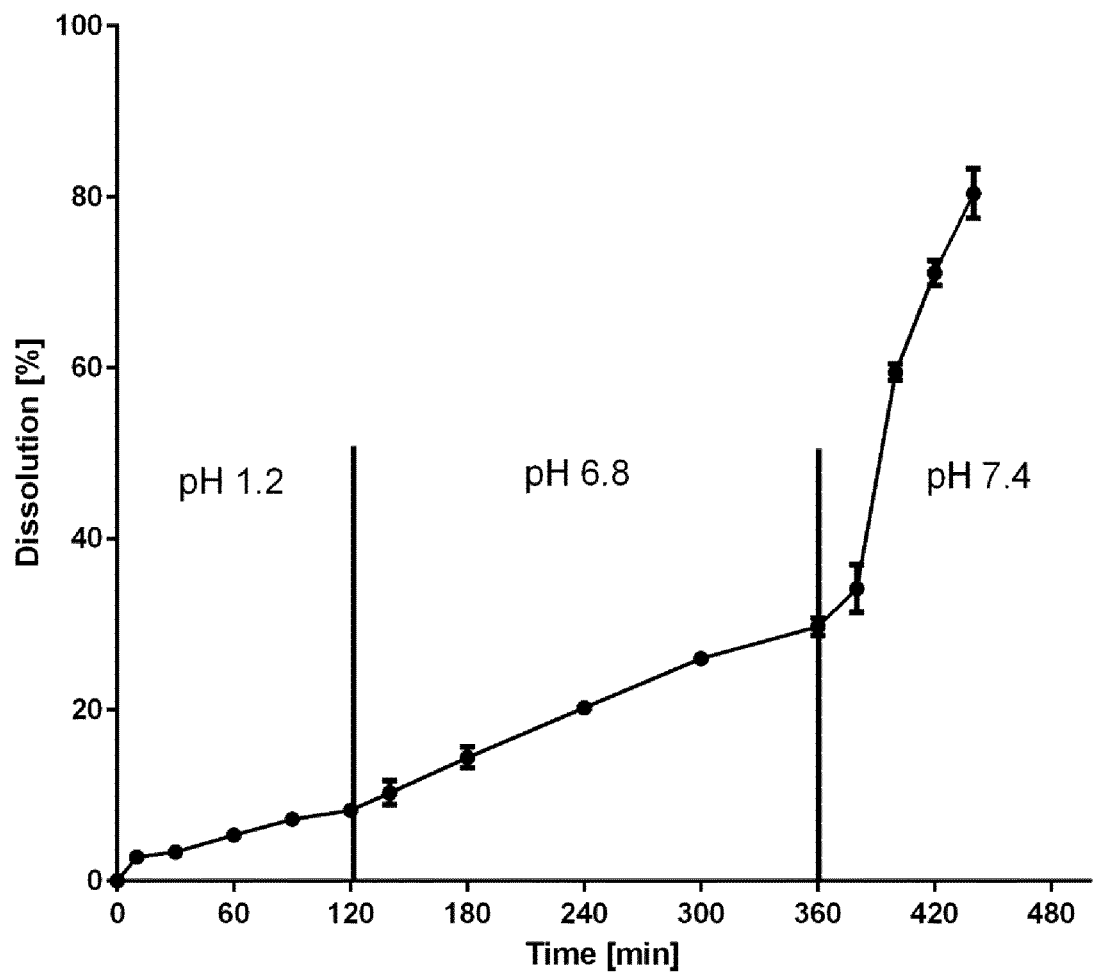
FIG. 5 shows the complete release profile of granules composed of 350-μm cellets with 0.5% nicotinic acid (NA), a subcoat of 9% trehalose and 1% citric acid and a final coat of 20% shellac in a dissolution testing setup using a Pharmatest DT 70 basket apparatus at 50 rpm. Simulated gastric fluid pH 1.2 (2 h) was followed by simulated intestinal fluids pH 6.8 (4 h) and pH 7.4 (2 h).

As shown in FIG. 5, a food grade enteric coating of NA using 20% shellac is feasible. The release of NA is triggered by elevated pH and starts at pH 6.8, with a burst at pH 7.4. By applying different kinds of subcoatings like citric acid with trehalose, the burst can be shifted to a higher or lower pH value and can thus be adjusted.

Figure 6:
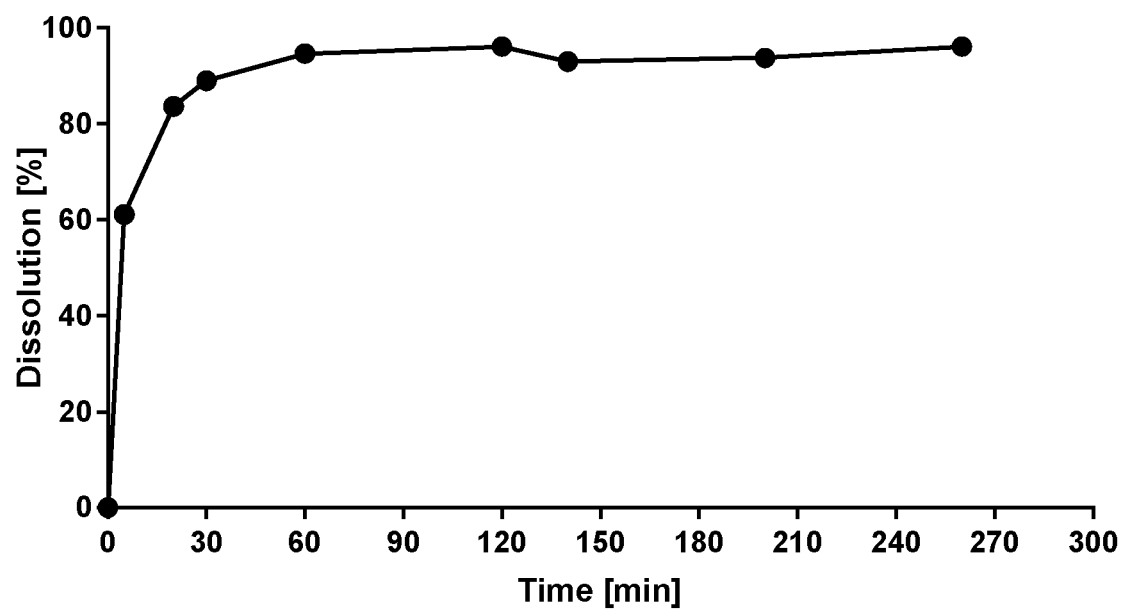
FIG. 6 shows the burst release of NA from granules composed of 350-μm cellets with 0.5% nicotinic acid (NA), a subcoat of 9% trehalose and 1% citric acid and a final coat of 25% shellac in a dissolution testing setup using a Pharmatest DT 70 basket apparatus at 50 rpm. Simulated intestinal fluid at pH 7.4 was used until all NA was released. Tmax (full release) was approximately 60 min, whereas a 50% release (t50) was already achieved after 10 min.

FIG. 6 shows the dissolution of similar NA granules with a shellac coating of 25% in SIF pH 7.4 for approximately 5 h, demonstrating the fast release of NA triggered by elevated pH. The time of maximum release (tmax) was found to be approximately 60 min, whereas half of the NA concentration (t50) was already released after 10 min. Using such formulations, a targeted delivery of NA or NAM to the lower small intestine, particularly to the terminal ileum, and the colon can be advantageously achieved.

In conclusion, a food grade enteric coating for NA using shellac with different subcoatings results in granules showing controlled and delayed release in dissolution testing. The release profile can be appropriately adapted by applying different kinds of subcoatings.

The examples above serve to explain the invention, but are not intended to limit the scope.

The invention claimed is:

1. A pharmaceutical composition for beneficially influencing blood and/or plasma and/or serum lipid levels by beneficially modifying the intestinal microbiota, comprising an active substance selected from nicotinic acid, nicotinamide, nicotinic acid esters, and combinations of any two or more thereof, wherein the composition is formulated for oral administration with controlled and/or delayed release for selective local release of the active substance for topical efficacy in the lower small intestine and/or colon where the intestinal microbiota to be modified are located, thereby beneficially modifying the intestinal microbiota, in an amount effective to increase high density lipoprotein (HDL) blood levels, decrease liver fat content, and/or beneficially influence blood and/or plasma and/or serum lipid levels, wherein the composition is provided with a coating and wherein the controlled and/or delayed release is achieved by the coating.

2. The composition of claim 1, wherein the composition is formulated for selective local release of the active substance for topical efficacy in the terminal ileum and/or colon.

3. The composition of claim 1, formulated for oral administration to provide controlled and/or delayed release of the active substance for local efficacy in the lower small intestine and/or colon.

4. The composition of claim 1, formulated for oral administration to provide controlled and/or delayed release of the active substance for local efficacy in the terminal ileum and/or colon.

5. The composition according to claim 1, formulated in a finished dosage form with an active substance content of 1-3000 mg per active substance per finished dosage form.

6. The composition according to claim 1, formulated in a finished dosage form with an active substance content of 10-2500 mg per active substance per finished dosage form.

7. The composition of claim 1, further comprising one or more of acetylsalicylic acid, a prostaglandin D2 antagonist, and a statin.

8. The composition of claim 1, further comprising a statin selected from atorvastatin, cerivastatin, fluvastatin, lovastatin, mevastatin, pitavastatin, pravastatin, rosuvastatin and simvastatin.

9. The composition of claim 1, wherein the pharmaceutical composition is selected from the group consisting of (i) a controlled and/or delayed release formulation of nicotinic acid; (ii) a controlled and/or delayed release formulation of nicotinamide, and (iii) a combination composition comprising a controlled and/or delayed release formulation of nicotinic acid and a controlled and/or delayed release formulation of nicotinamide, wherein the combination composition may be a fixed dose combination composition or a variable dose combination composition.

10. The composition of claim 1, wherein the active substance is formulated such that, after administration of the composition, blood, plasma and/or serum levels of the active substance do not exceed two orders of magnitude higher than levels before administration.

11. The composition of claim 1, wherein the active substance is formulated such that, after administration of the composition, blood, plasma and/or serum levels of the active substance do not exceed one order of magnitude higher than levels before administration.

12. The composition of claim 1, wherein the active substance is formulated such that, after administration of the composition, any increase in blood, plasma and/or serum levels of the active substance occurs with a longer latency time as compared to that occurring after administration of the same amount of unformulated active substance.

13. The composition of claim 1, wherein the active substance is formulated such that, after administration of the composition, any increase in blood, plasma and/or serum levels of the active substance is at least 50% lower as compared to that occurring after administration of the same amount of unformulated active substance.

14. A method of influencing blood, plasma and/or serum lipid levels in a subject in need thereof, comprising administering to the subject a composition according to claim 1.

15. A method for the therapy of a disease and/or syndrome associated with and/or accompanied by unfavorable or abnormal or imbalanced blood and/or plasma and/or serum lipid levels selected from lipid metabolism disorders, dyslipidemia, non-alcoholic fatty liver disease (NAFLD), non-alcoholic steatohepatitis (NASH), cardiovascular diseases, arteriosclerosis, atherosclerosis, metabolic syndrome, and obesity, and diseases and/or conditions associated with unfavorable or abnormal blood and/or plasma and/or serum lipid levels which partly or entirely result from unfavorable or abnormal changes or imbalances in the intestinal microbiota and/or an impaired interaction between intestinal microbiota and intestines, comprising orally administering a composition according to claim 1 to a subject in need thereof.

16. A pharmaceutical composition for beneficially influencing blood and/or plasma and/or serum lipid levels by beneficially modifying the intestinal microbiota, comprising an active substance selected from nicotinic acid, nicotinamide, nicotinic acid esters, and combinations of any two or more thereof, wherein the composition is provided with a coating resistant to gastric juice that dissolves depending on the pH and/or a film coating, wherein the composition is formulated for oral administration with controlled and/or delayed release for selective local release of the active substance for topical efficacy in the lower small intestine and/or colon where the intestinal microbiota to be modified are located, thereby beneficially modifying the intestinal microbiota, in an amount effective to increase high density lipoprotein (HDL) blood levels, decrease liver fat content, and/or beneficially influence blood and/or plasma and/or serum lipid levels, and wherein the controlled and/or delayed release is achieved by the coating.

17. The composition of claim 16, wherein the composition is formulated for selective local release of the active substance for topical efficacy in the terminal ileum and/or colon.

18. The composition of claim 16, formulated for oral administration to provide controlled and/or delayed release of the active substance for local efficacy in the lower small intestine and/or colon.

19. The composition of claim 16, formulated for oral administration to provide controlled and/or delayed release of the active substance for local efficacy in the terminal ileum and/or colon.

20. The composition according to claim 16, formulated in a finished dosage form with an active substance content of 1-3000 mg per active substance per finished dosage form.

21. The composition according to claim 16, formulated in a finished dosage form with an active substance content of 10-2500 mg per active substance per finished dosage form.

22. The composition of claim 16, further comprising one or more of acetylsalicylic acid, a prostaglandin D2 antagonist, and a statin.

23. The composition of claim 16, further comprising a statin selected from atorvastatin, cerivastatin, fluvastatin, lovastatin, mevastatin, pitavastatin, pravastatin, rosuvastatin and simvastatin.

24. The composition of claim 16, wherein the pharmaceutical composition is selected from the group consisting of (i) a controlled and/or delayed release formulation of nicotinic acid; (ii) a controlled and/or delayed release formulation of nicotinamide, and (iii) a combination composition comprising a controlled and/or delayed release formulation of nicotinic acid and a controlled and/or delayed release formulation of nicotinamide, wherein the combination composition may be a fixed dose combination composition or a variable dose combination composition.

25. The composition of claim 16, wherein the active substance is formulated such that, after administration of the composition, blood, plasma and/or serum levels of the active substance do not exceed two orders of magnitude higher than levels before administration.

26. The composition of claim 16, wherein the active substance is formulated such that, after administration of the composition, blood, plasma and/or serum levels of the active substance do not exceed one order of magnitude higher than levels before administration.

27. The composition of claim 16, wherein the active substance is formulated such that, after administration of the composition, any increase in blood, plasma and/or serum levels of the active substance occurs with a longer latency time as compared to that occurring after administration of the same amount of unformulated active substance.

28. The composition of claim 16, wherein the active substance is formulated such that, after administration of the composition, any increase in blood, plasma and/or serum levels of the active substance is at least 50% lower as compared to that occurring after administration of the same amount of unformulated active substance.

29. A method of influencing blood, plasma and/or serum lipid levels in a subject in need thereof, comprising administering to the subject a composition according to claim 16.

30. A method for the therapy of a disease and/or syndrome associated with and/or accompanied by unfavorable or abnormal or imbalanced blood and/or plasma and/or serum lipid levels selected from lipid metabolism disorders, dyslipidemia, non-alcoholic fatty liver disease (NAFLD), non-alcoholic steatohepatitis (NASH), cardiovascular diseases, arteriosclerosis, atherosclerosis, metabolic syndrome, and obesity, and diseases and/or conditions associated with unfavorable or abnormal blood and/or plasma and/or serum lipid levels which partly or entirely result from unfavorable or abnormal changes or imbalances in the intestinal microbiota and/or an impaired interaction between intestinal microbiota and intestines, comprising orally administering a composition according to claim 16 to a subject in need thereof.

* * * * *